United States Patent [19]

Tamburini et al.

[11] Patent Number: 5,138,048

[45] Date of Patent: Aug. 11, 1992

[54] 4-(2-OXO-CYCLOHEXYL) AZETIDINONES

[75] Inventors: Bruno Tamburini, San Pietro in Cariano; Alcide Perboni, San Giorgio di Mantova; Tino Rossi, Verona; Daniele Donati, Soave; Daniele Andreotti, Tresigallo; Giovanni Gaviraghi, Verona; Stefano Biondi, Rimini; Claudio Bismara, Oppeano, all of Italy

[73] Assignee: Glaxo S.p.A., Verona, Italy

[21] Appl. No.: 578,949

[22] Filed: Sep. 7, 1990

[30] Foreign Application Priority Data

Sep. 8, 1989 [GB] United Kingdom ............... 8920337
Jul. 13, 1990 [GB] United Kingdom ............... 9015484

[51] Int. Cl.$^5$ .................. C07F 7/18; C07D 205/08; C07D 487/04; C07D 477/00
[52] U.S. Cl. ..................................... 540/200; 540/302
[58] Field of Search ........................................ 540/200

[56] References Cited

FOREIGN PATENT DOCUMENTS

0422596A2 4/1991 European Pat. Off. .
61-236785 10/1986 Japan .

OTHER PUBLICATIONS

*Tetrahedron Letters*, 23, 4, 379–382, 1982.
*Heterocycles*, 25, 221–227, 1987.
*Tetrahedron Letters*, 28, 5, 507–510, 1987.
*Tetrahedron Letters*, 27, 47, 5687–5690, 1986.

*Primary Examiner*—Mark L. Berch
*Attorney, Agent, or Firm*—Bacon & Thomas

[57] ABSTRACT

Compounds of the general formula (I)

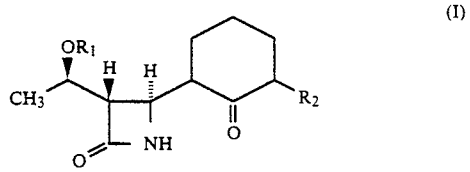

in which:

$R_1$ represents a hydroxyl protecting group; and
$R_2$ represents a hydrogen or halogen atom, an azido group, a $C_{1-3}$ alkyl group, a group $(CH_2)_m OR_3$ wherein m is zero or one and $R_3$ represents a hydrogen atom or a hydroxyl protecting group, an azidoethoxy group, a protected hydroxyethoxy group or a group $XR_4$ in which X is an oxygen atom or the group $S(O)_n$ in which n is zero, 1 or 2 and $R_4$ represents a $C_{1-5}$alkyl, $C_{3-7}$cycloalkyl or phenyl group or when X is oxygen or sulphur then $R_4$ may also represent the group $AlkNR_5R_6$ in which Alk represents a $C_{2-6}$ straight or branched alkylene chain and $R_5$ and $R_6$ independently represent a hydrogen atom or $C_{1-4}$alkyl group or $R_5$ and $R_6$ together with the nitrogen atom to which they are attached form a pyrrolidino or piperidino ring or the group $NR_5R_6$ represents a protected amino group, or $R_2$ represents the group $(CH_2)_m NR_7R_8$ in which m is zero or 1 and $R_7$ and $R_8$ independently represent a hydrogen atom or a $C_{1-4}$alkyl group or $NR_7R_8$ represents a protected amino group, or $R_2$ and the carbon atom to which it is attached represent a keto group or a ketal derivative thereof; and acid addition salts of such compounds containing basic centers.

13 Claims, No Drawings

4-(2-OXO-CYCLOHEXYL) AZETIDINONES

This invention relates to novel heterocyclic compounds useful in the preparation of compounds having antibacterial activity, and to processes for their preparation.

Thus the present invention provides compounds of the general formula (I)

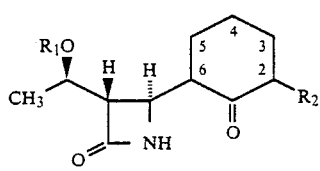
(I)

in which $R_1$ represents a hydroxyl protecting group;

$R_2$ represents a hydrogen or halogen atom, an azido, or $C_{1-3}$alkyl group, or a group $(CH_2)_mOR_3$ wherein m is zero or one and $R_3$ represents a hydrogen atom an hydroxyl protecting group or $R_2$ represents an azidoethoxy or protected hydroxyethoxy group or $R_2$ represents a group $XR_4$ in which X is an oxygen atom or the group $S(O)_n$ in which n is zero, 1 or 2 and $R_4$ represents a $C_{1-5}$alkyl, $C_{3-7}$cycloalkyl or phenyl group or when X is oxygen, or sulphur then $R_4$ may also represent the group Alk $NR_5R_6$ in which Alk represents a $C_{2-6}$ straight or branched alkylene chain and $R_5$ and $R_6$ independently represent a hydrogen atom or $C_{1-4}$alkyl group or $R_5$ and $R_6$ together with the nitrogen atom to which they are attached form a pyrrolidino, or piperidino ring or the group $NR_5R_6$ represents a protected amino group or $R_2$ represents the group $(CH_2)_mNR_7R_8$ in which m is zero or 1 and $R_7$ and $R_8$ independently represent a hydrogen atom or a $C_{1-4}$alkyl group or or $NR_7R_8$ represents a protected amino group or $R_2$ and the carbon atom to which it is attached represents a keto group or a ketal thereof.

In addition to the fixed stereochemical arrangement as defined in formula (I) the molecule contains a further asymmetric carbon atom at the 6-position, and another at the 2-position, except when $R_2$ is a hydrogen atom or when $R_2$ and the carbon atom to which it is attached forms a keto group or a ketal derivative thereof. It will be appreciated that all stereoisomers including mixtures thereof arising from these additional asymmetric centres, are within the scope of the compounds of formula (I).

When the group $R_2$ contains a basic centre acid addition salts of such compounds are also included in the invention.

Suitable hydroxyl protecting groups $R_1$ include those which may be removed by hydrolysis under buffered conditions or under non-aqueous conditions. Thus the group $OR_1$ may be a an ether or an acyloxy group. Examples of particularly suitable ethers include those in which $R_1$ is a hydrocarbylsilyl group such as trialkylsilyl, e.g. trimethylsilyl or t-butyldimethylsilyl. When the group $OR_1$ represents an acyloxy group then examples of suitable groups $R_1$ includes alkanoyl e.g. acetyl, pivaloyl, alkenoyl e.g. allylcarbonyl, aroyl e.g. p-nitrobenzoyl, alkoxycarbonyl e.g. t-butoxycarbonyl, haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or P- nitrobenzyloxycarbonyl, or alkenyloxycarbonyl e.g. allyloxycarbonyl.

A particularly convenient protecting group $R_1$ is t-butyldimethylsilyl.

When the group $R_3$ is or contains a hydroxyl protecting group then conveniently the protecting group is a group as defined above for $R_1$. When the group $NR_5R_6$ or $NR_7R_8$ is a protected amino group this is preferably a group that may be converted into the required amino group under buffered conditions or non-aqueous conditions. A particularly suitable amino protecting group is the allyloxycarbonyl group.

The general formula (I) as drawn includes at least 4 stereoisomers and mixtures thereof and the individual isomers may be represented by formula (1a, 1b, 1c and 1d).

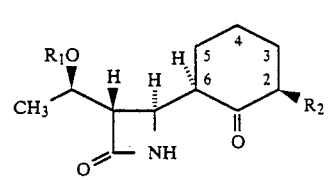
(1a)

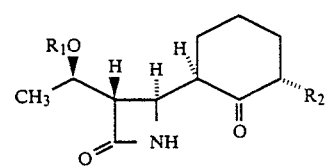
(1b)

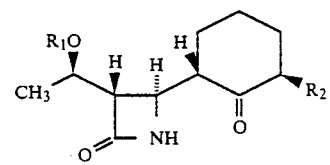
(1c)

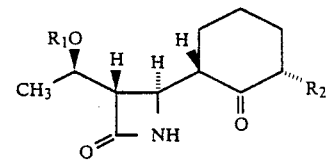
(1d)

The wedge shaped bond indicates the bond is above the plane of the paper The broken bond indicates that the bond is below the plane of the paper.

The configuration shown for the carbon atom at the 6- position in formulae 1a and 1b is hereinafter referred to as the β-configuration and in formulae 1c and 1d as the α-configuration.

The configuration shown at the carbon atom at the 2 position in formulae 1a and 1c is hereinafter referred to as the β-configuration and in formulae 1b and 1d as the α-configuration.

In general in the specific compounds named below the β-configuration at the 6 position corresponds to the R isomer and the α-configuration corresponds to the S isomer. At the 2-position the β isomer corresponds to the R isomer except when the group $R_2$ is an hydroxylalkyl e.g. hydroxymethyl group then it is the S isomer. The α-configuration at the 2-position corresponds to the S isomers except when $R_2$ is an hydroxyalkyl group when it is the R isomer.

A preferred group of compounds for formula (I) are those wherein $R_2$ represents a halogen atom e.g. iodine, a hydrogen atom or, an azido, $C_{1-3}$alkoxy e.g. methoxy or ethoxy, isopropoxy, cyclopentyloxy, $C_{1-3}$alkylthio e.g. methylthio, phenylthio, aminoalkoxy e.g. aminoethoxy, protected aminoethoxy e.g. allyloxycarbonylaminoethoxy, amino, protected amino e.g. allyloxycarbonylamino, alkylamino, e.g. methylamino, protected alkylamino, aminomethyl, protected aminomethyl e.g. allyloxycarbonylaminomethyl, azidoethoxy, protected hydroxyethoxy e.g. benzyloxy, ethoxy, or trimethylsilyloxyethoxy, hydroxy, protected hydroxy e.g. trialkylsilyloxy, or protected hydroxymethyl e.g. trialkylsilyloxymethyl.

A particularly preferred group of compounds of formula (I) are those where $R_2$ represents a hydrogen atom or a methoxy group.

A particularly preferred group of compounds of formula (I) are the stereoisomers with the $6\beta$, $2\alpha$ configuration as represented by formula (1b).

Within the groups of preferred and particularly preferred compounds those wherein $R_1$ represents a trialkylsilyl group e.g. t-butyldimethylsilyl are especially preferred.

Compounds of formula (I) may be prepared by treating the azetidinone (II) with the enolate ion of the ketone (III).

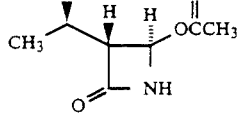

(II)

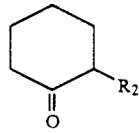

(III)

The reaction is preferably carried out at a low temperature e.g. $-78°$ C. in a solvent such as tetrahydrofuran.

The enolate ion of the ketone (III) is conveniently generated in situ by treatment with a suitable base such as lithium bis(trimethyl silyl)amide.

Alternatively the compounds formula (I) may be prepared from the reaction of azetidinone (II) with the enol ether (IV)

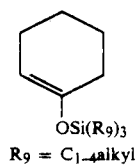

(IV)

$R_9 = C_{1-4}$alkyl

The reaction may be carried out in a solvent such as methylene chloride in the presence of an activated ester of trifluoromethanesulphonic acid e.g. the trimethylsilyl ester or a Lewis acid such as stannic chloride.

Compounds of formula (I) may also be prepared by reduction of a compound of formula (V)

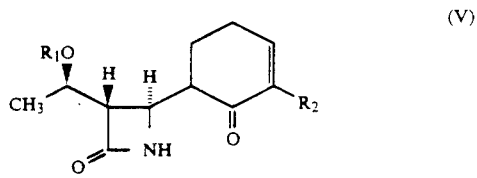

(V)

The reduction may be effected using hydrogen and a metal catalyst e.g. palladium on a suitable support e.g. carbon or aluminia. The reaction is carried out in a solvent such as an ester e.g. ethyl acetate.

The compound of formula (V) may be prepared from the reaction of the azetidinone (II) with the ketone (VI) or the enol ether (VII) using the conditions described above for preparing compounds of formula (I) from the ketone (III) and the enol ether (IV).

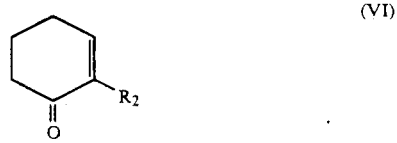

(VI)

(VII)

Compounds of formula (I) may also be prepared by oxidation of the alcohol of formula (VIII)

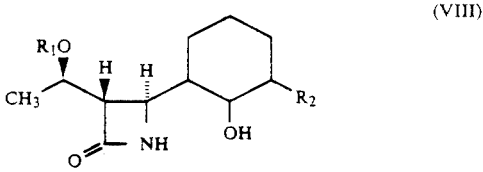

(VIII)

in which the groups $R_1$ and $R_2$ have the meanings defined above. The oxidation may be carried out using a conventional oxidising agents known in the art for converting a cyclohexanol into a cyclohexanone. Thus for example the oxidation may be carried out using pyridinium chlorochromate. The reaction is preferably carried out in a solvent such as methylene chloride.

The alcohol (VIII) may be prepared by reduction of the $\alpha$-$\beta$ unsaturated ketone (V). This reduction is conveniently carried out in a two stage reaction. The first stage is the reduction of the ketone to the alcohol using a suitable metal hydride such as sodium borohydride. The resultant $\alpha$-$\beta$ unsaturated alcohol is then reduced to the required alcohol (VIII) using hydrogen and a metal catalyst as described above for the preparation of the ketone (I) from the $\alpha$-$\beta$ unsaturated ketone (V).

Compounds of formula (I) in which $R_2$ represents an alkyl-thio group may be prepared by treating the corresponding compound of formula (I) in which $R_2$ represents a hydrogen atom with an alkali metal base e.g. lithium bis(trimethylsilyl)amide and the corresponding alkylthio methanesulphonate.

In this reaction an alkylthio group is introduced on to the N-nitrogen atom of the azetidinone group and thus it is necessary to use two equivalents of the base lithium bis(trimethylsilyl amide) and the corresponding alkylthio methanesulphonate. If the reaction is carried out stepwise, such that the alkylthio group is introduced on the azetidinone nitrogen before the second equivalent of base and alkylthio reagent is added, then the reaction gives predominantly one stereoisomer at the 4-position. If however the 2 equivalents of base and alkylthio ester are added together then the reaction gives an approximately even mixture of the two stereoisomers at the 4-position. The alkylthio group on the azetidinone nitrogen atom may be removed by treatment with a suitable nucleophile e.g. 2-mercaptopyridine in the presence of an additional tertiary organic base such as triethylamine, to give the required compound of formula (I) in which $R_2$ represents an alkylthio group.

In a modification of this process the compound of formula (I) in which $R_2$ represents hydrogen may be first converted into an alternative N-protected derivative e.g. the N-trimethylsilyl derivative by conventional means and then the alkylthio group ($R_2$) introduced using the conditions described above followed by subsequent removal of the N-protecting group.

Compounds of formula (I) in which the group $R_2$ has the meaning $SR_4$ may also be prepared form a corresponding compound in which $R_2$ represents hydrogen, via a corresponding halo deriivative. Thus for example reaction of a compound of formula (I) in which $R_2$ is hydrogen with a suitable base such as sodium or lithium bis(trimethyl- silyl) amide in a solvent such as hexane and/or tetrahydrofuran followed by reaction with iodine and then sodium sulphite gives the corresponding iodo derivative I(I;$R_2$=I). Treatment of the iodide with the thiol $R_2$SH in aqueous methylene chloride in the presence of a suitable base such as a phase transfer catalyst e.g. tetrabutylammonium hydroxide gives the required compound (I: $R_2$=$SR_4$).

The compound of formula (I) wherein $R_2$ represents an azidoethoxy group maybe prepared by treating a compound of formula (I) in which $R_2$ represents a benzyloxyethoxy group with an azide such as sodium azide in the presence of a triarylphosphine. The reaction is preferably carried out in the presence of an aprotic solvent such as dimethylformamide.

The compound of formula I in which $R_2$ is an amino or aminoethoxy group may be prepared by reduction of the corresponding compound of formula (I) in which $R_2$ is an azido or an azidoethoxy group.

The reduction may be conveniently carried out using hydrogen and a metal catalyst such as a palladium catalyst in a solvent such as ethyl acetate.

The compound of formula (I) in which $R_2$ is a protected amino group may be prepared from a compound of formula (I) in which $R_2$ is a primary amino group. Thus for example the compound of formula (I) in which $R_2$ is an allyloxcarbonylamino group may be prepared by treating the primary amine with allyloxcarbonyl chloride. The reaction is preferably carried out in the presence of a tertiary organic base such as pyridine and in a solvent such as ethyl acetate.

The alcohol of formula (VIII) in which $R_2$ is an alkoxy group may be prepared by reacting the corresponding epoxide (IX) with the corresponding alcohol $R_4$OH in the presence of an acid catyst such as p-toluene sulphonic acid.

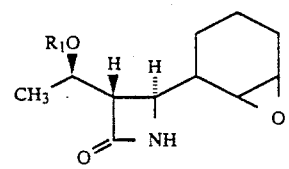

(IX)

The alcohol of formula (VIII) in which $R_2$ is an azido group may be prepared by treating the expoxide (IX) with an alkali metal azide. The reaction is preferably carried out in a solvent such as a alkanol e.g. methanol.

The alcohol of formula (VIII) in which $R_2$ is an aminomethyl group may be prepared by the reaction of the expoxide (IX) with an alkali metal cyanide followed by reduction of the cyano derivative thus obtained.

The alcohol of formula (VIII) in which $R_2$ is the group $NR_7R_8$ wherein $R_7$ is a hydrogen atom or a $C_{1-4}$alkyl group and $R_8$ represents a $C_{1-4}$alkyl group may be prepared by from the rection of the epoxide (IX) with the corresponding amine $R_7R_8$NH. The reaction is preferably carried out in a solvent such as an alkanol ethanol or aqueous ethanol and in the presence of an ammonium salt.

The alcohol of formula (VIII) in which $R_2$ is a protected secondary amino group or protected aminomethyl group may be prepared fron the corresponding secondary amino group —$NHR_8$ or aminomethyl group by conventional means, such as for example reaction with a suitable acid chloride e.g. allyloxycarbonylchloride.

The epoxide formula (IX) may be prepared by epoxidation of the cycloalkene of formula (X)

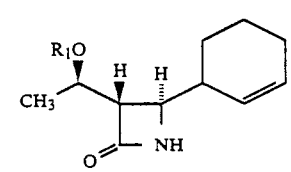

(X)

in which $R_1$ has the meanings given above. The epoxidation may conveniently be carried out by treating the cycloalkene of formula (X) with a peracid. Suitable peracid include optionally substituted perbenzoic acids such as perbenzoic acid or meta chloroperbenzoic acid, and peralkanoic acids such as peracetic acid and trifluoroperacetic acid. The reaction may be carried out in a solvent such as a halohydrocarbon e.g. dichloromethane and conveniently at a temperature within the range $-30°$ to $+30°$ C.

The cycloalkene of formula (X) may be prepared by treating the corresponding tosylhydrazone (XI)

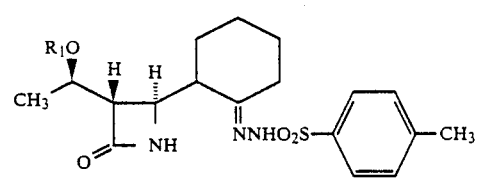

(XI)

in which $R^1$ is a hydroxyl protecting group with a base, such as lithium diisopropylamide. The reaction is conveniently carried out in an aprotic solvent such as an ether e.g. tetrahydrofuran and at a temperature between −50° C. to 0° C.

The tosylhydrazone (XI) may be prepared by treating a compound of formula (I)

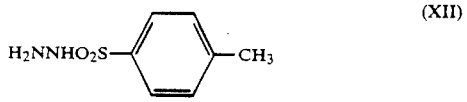
(XII)

in which R₁ is a hydroxyl protecting group and R₂ is hydrogen with tosylhydrazide (XII) in a suitable solvent such as glacial acetic acid.

The compounds of formula (I) are useful intermediates in the preparation of compounds which possess antibacterial activity. Thus for example they are intermediates for the parparation of compounds of formula (XIII)

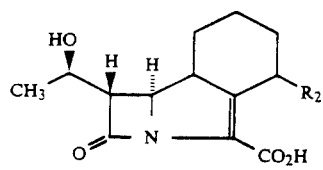
(XIII)

in which R₂ has the meanings given above and salts thereof. These compounds exhibit a broad spectrum of antibacterial activity against a wide range of pathogenic microorganisms and have a high resistance to β-lactamases.

The compounds of formula (XIII) may be prepared by treating a compound of formula (I) with an activated derivative of the acid (XIV) HOOCCO₂R$_a$ in which R$_a$ is a carboxyl protecting group e.g. an allyl group. Suitable activated derivatives of the acid (XIV) include the corresponding acid chloride. This may be reacted with compound in the presence of a tertiary base such as pyridine or a trialkylamine in an aprotic solvent such as dichloromethane.

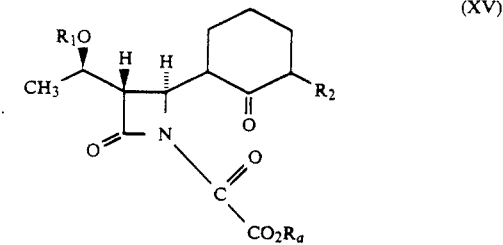
(XV)

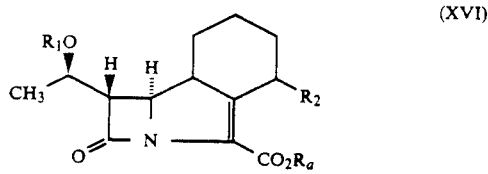
(XVI)

The resultant oxalamide (XV) is then cyclised to give the tricyclic compound (XVI) by heating in the presence of an organic phosphite. Suitable organic phosphites include triethylphosphite and the reaction is preferably carried out in a solvent at a temperature within the range 60°-200°.

The tricyclic compound (XVI) may then be converted into a required compound (XV) by removal of the protecting groups R₁ and R$_a$ using well known conventional procedures.

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to °C.

Infrared spectra were measured in chloroform-dl solutions on a FT-IR instrument. Proton Magnetic Resonance (1H-NMR) spectra were recorded at 300 MHz as solutions in chloroform-d₁. Chemical shifts are reported in ppm downfield (δ) from Me₄Si, used as an internal standard, and are assigned as singlets (s), doublets (d), doublet of doublets (dd) or multiplets (m).

Column chromatography was carried out over silica gel (Merck AG Darmstadt, Germany).

Solutions were dried over anhydrous sodium sulphate.

"Petrol" refers to petroleum ether, b.p. 40°-60° C.

Methylene chloride was redistilled over calcium hydride; tetrahydrofuran was redistilled over sodium; ethyl ether was redistilled over sodium; xylene was redistilled over phosphorus pentoxide and ethyl acetate was dried over activated molecular sieves.

INTERMEDIATE 1

(3S,4R)-3-[(R)-1-(t-Butylidmethylsilyloxy)ethyl]-4-((R)-2′-(1-oxocyclohexyl))]-1-methylthioazetidin-2-one Example 1a (9.56 g) was dissolved in tetrahydrofuran (60 ml) under nitrogen and cooled to −78° C. Lithium bis(trimethylsilyl)amide (32.3 ml 1M solution in hexane) was added in 8 min from a dropping funnel and the reaction stirred at −78° for 30 min. Methylthiomethyl sulphonate (4.08 g) was added, the mixture keep at −78° C. for 30 min and then warmed to −30° C. Ethyl ether (20 ml) was added and the mixture was maintained at −30° C. for 30 min and poured in to a saturated solution of ammonium chloride (100 ml). The organic layer was washed with a 1% solution of cold hydrochloric acid (2×50 ml) then with brine (50 ml). The oil obtained after evaporation of the organic solvent was chromatographed (eluants E/P) to yield the title compound (5.15 g).

IR (CDCl₃) ν$_{max}$ (cm⁻¹) 1765 (β-lactam), 1709 (c=O), 2850 and 1300 (—S—CH₃)

H¹-NMR (CDCl₃): 4.307 (dd), 4.22 (m), 2.992 (t), 2.61 (m), 2.46 (m), 2.395 (s), 2.407 (m), 2.105 (m), 1.935 (m), 1.70 (m), 1.49 (m), 1.19 (d), 0.86 (s), 0.064 (s), 0.048 (s).

INTERMEDIATE 2

(3S,4R)-3-[(R)-1-(t-Butyldimethylsilyloxy)ethyl]-4-((R)-2′-((S)-6′-methylthio-1′-oxocyclohexyl)]-1-methylthioazetidin-2-one A 1M solution in hexane of lithium bis(trimethylsilyl)amide (18 ml) was cooled at −78° and a solution of intermediate 1 (5.15 g) in tetrahydrofuran (20 ml) added over 4 min. The resulting mixture was stirred for 30 min the methylthio methanesulphonate (2.27 g) was added. The reaction mixture was kept at −78° for 30 min then at −30° C. for 10 min. Diethyl ether (50 ml) was added and the mixture was poured into a saturated solution of ammonium chloride (200 ml). The organic layer was washed with cold 1% hydrochloric acid (2×100 ml)

then with brine (100 ml). The organic layer was dried, evaporated under reduced pressure and purified by flash chromatography (eluants EE/P) to obtain the title compound (3.72 g) as a yellow oil.

IR (CDCl$_3$) $\nu_{max}$ (cm$^{-1}$) 1757 ($\beta$-lactam), 1699 (C=O)

H$^1$-NMR (CDCl$_3$): 4.396 (m), 4.18 (m), 3.5 (m), 3.03 (dd), 2.42 (s), 2.2 (m), 2.068 (s), 2.1-1.6 (m), 1.47 (d), 1.21 (d), 0.86 (s), 0.077 (s), 0.065 (s).

INTERMEDIATE 3

(3S,4R)-3-[(R)-1-(t-Butyldimethylsilyloxy)ethyl]-4-((S)-2'-((R)-6'-methylthio-1'-oxocyclohexyl))-1-methylthi-oazetidin-2-one (3a) and
(3S,4R)-3-[(R)-1-(t-Butylmethylsilyloxyethyl]-4((S)-2'-((S)-6'-methylthio-1'-oxo-cyclohexyl)-1-methylthi-oazetidin-2-one (3b)

A 1M solution in hexane of lithium bis(trimethylsilyl-)amide (18 ml) was cooled at $-78°$ under nitrogen and a solution of Example 1b (2 g) in tetrahydrofuran (20 ml) was added.

During the addition the temperature rose to $-70°$ C. The reaction mixture was kept under stirring at $-78°$ for 30 min then methylthio methanesulphonate (2 ml) was carefully added over 5 min. After a further 15 min under stirring the mixture was allowed to warm to $-30°$ C. for 1 h and then diluted with anhydrous diethylether (40 ml). The mixture was poured into a saturated aqueous solution of ammonium chloride (200 ml). The organic layer was washed with a 1% cold solution of hydrochloric acid (2×50 ml) then with brine (50 ml) and dried. The organic layer was evaporated and the residue purified by flash chromatography (eluting with petroleum ether/diethylether) to give the title compound 3a (1 g). (t.l.c. Rf=0.7 eluants P/EE 3/7). Further elution gave the title compound 3b (0.84 g) as a yellow oil (t.l.c. Rf 0 0.35 eluants P/EE 3/7).

INTERMEDIATE 3a

IR (CDCl$_3$) $\nu_{max}$ (cm$^{-1}$) 1757 ($\beta$-lactam), 1725 (C=O)

H$^1$-NMR (CDCl$_3$): 4.4 (dd), 4.2 (m), 3.6 (m), 2.9 (dd), 2.6 (m), 2.45 (m), 2.4 (s), 2.11 (s), 2.0-1.7(m), 1.9 (m), 1.2 (d), 0.8 (s), 0.04 (s).

INTERMEDIATE 3b

IR (CDCl$_3$) $\nu_{max}$ (cm$^{-1}$) 1755 ($\beta$-lactam), 1707 (C=O)

H$^1$-NMR (CDCl$_3$): 4.31 (dd), 4.24 (m), 3.52 (m), 3.33 (dd), 2.96 (dd), 2.45 (s). 2.17 (m), 2.12 (s), 2.1-1.9 (m), 1.75 (m), 1.46 (m), 1.18 (d), 0.86 (s), 0.06 (s).

INTERMEDIATE 4

(3S,4R)-1-(t-butyldimethylsilyl)-4-acetoxy-3[(R)-(t-butyldimethylsilyloxy)ethyl]azetidin-2-one To a stirred ice-cold solution of the (3S,4R)-4-acetoxy-3((R)-t-butyldimethylsilyloxy)ethyl)-2-azetidi-none (112 g) in dichloromethane (800 ml), t-butyldimethylchlorosilane (73 g) and triethylamine (80 ml) were added. The mixture was stirred at room temperature for 20 hours then washed with water (1 l) and brine (300 ml). The organic layer was dried and evaporated to give an oil (160 g) which was dissolved in a mixture of cyclo-exane/ethyl acetate (95/5) (1600 ml) and treated with silica gel (480 g). The suspension was stirred for 15 min then filtered. The solid was washed with cyclohex-ane/ethyl acetate (95/5:4.81) and the solvent evaporated to give the title compound (110 g) as a pale yellow oil. (Rf=0.85 Petrol/Diethyl ether=2/1)

IR(CDCl$_3$)V$_{max}$ (cm$^{-1}$): 1747(C=O)

H$^1$-NMR a (CDCl$_3$):6.14(d), 4.15(m), 3.07(dd), 2.03(s), 1.2(d), 0.9(s), 0.84(s), 0.22(s), 0.055(s), 0.35(s), 0.005(s)ppm.

INTERMEDIATE 5

(3S,4R)-1-(t-butyldimethylsilyl)3-[(R)-1-(t-butyldimethylsilyloxy)ethyl]-4-[2'-(1'-oxo-cycxlohexyl]azetidin-2-one Stannic chloride (35.4 ml) was added dropwise to stirred acetonitrile (400 ml) under nitrogen atmosphere at $-40°$ C., a white solid formed together with white fumes which were eliminated by nitrogen flushing. The obtained suspension was allowed to rise to $-10°$ C. then a solution of 1-trimethylsilyloxycyclohexene (60.6 ml) and compound of Intermediate 4 (110 g) in acetonitrile (300 ml) was added in 10 minutes. The yellow solution was stirred at 0° C. for 10 min then poured into a stirred, ice-cold, mixture of a 10% aq solution of sodium hydroxide (1 l), diethyl ether (1 l) and ice (500 g). The organic layer was separated, washed again with sodium hydroxide (500 ml) and then with a saturated solution of ammonium chloride, dried and evaporated to give a yellow solid (117.7 g). The solid was dissolved at 40° C. in isopropanol (300 ml) then cooled at room temperature, water (300 ml) was added slowly under stirring to obtain a solid which was stirred at 0° C. for 30 min then filtered, washed with a 1 to 1 mixture of isopropanol/-water (100 ml) and dried under vacuum at 40° C. for 15 hr to afford the title compound (76 g) as a mixture of 2'R and 2'S isomers in a ratio of 70% to 30% (the ratio between the two isomers was determined by HPLC using hexane/ethanol (99/1) as eluant).

INTERMEDIATE 6

(3S,4R)-1-(t-butyldimethylsilyl)-3-[(R)-1-(t-butyldimethylsilyloxy)ethyl]-4-[6'-(1'-trimethylsilyloxycyclohex-1'-enyl)]azetidin-2-one A 1M solution of lithium bis(trimethylsilyl)amide in hexane (70 ml) was added to tetrahydrofuran (150 ml), the mixture stirred under nitrogen, cooled to $-70°$ C. and then a solution of the compound of Intermediate 5 (15.5 g) in tetrahydrofuran (70 ml) was added over 20 min. The obtained solution was stirred for 30 min then chlorotrimethylsilane (10 ml) was added over 10 min. The reaction temperature was allowed to rise to $-20°$ C. then the mixture was poured into a saturated ammonium chloride solution (500 ml) and the resulting mixture extracted with diethyl ether (300 ml). The organic layer was washed with water (200 ml), a 2% ice-cold solution of hydrochloric acid (300 ml), aqueous solution of sodium hydrogen carbonate and brine, dried and evaporated under reduced pressure to give the title compound as a mixture of 6'R and 6'S isomers.

INTERMEDIATE 7

(3S,4R)-3-[(R)-1(t-butyldimethylsilyloxy)ethyl]-4-[(R)[2'-(S)-6'-hydroxy-1'-oxocyclohexyl]azetidin-2-one The compound of Intermediate 6 was dissolved at $-10°$ C. in dichloromethane (300 ml) and treated with sodium hydrogen carbonate (2.85 g). To the obtained suspension, 3-chloroperoxybenzoic acid (8.5 g) was added portionwise over 30 min. The reaction mixture was stirred at 0° C. for 1.5 h and at room temperature for 1 h then solid sodium sulphite (5 g) was added. After stirring for 30 min the solid was filtered and washed with dichloromethane (100 ml). The organic layer was washed with a 3% aqueous sodium sulphite solution (100 ml) followed by an ice-cold 3% aqueous sodium hydrogen carbonate solution (3×150 ml) and water, dried and evaporated to give a yellow oil which was dissolved in methanol (250 ml). Potassium fluoride (6 g) was added and the obtained solution stirred at room temperature for 30 min then poured into a saturated solution of ammonium chloride (500 ml) and the resulting mixture extracted with ethyl acetate (3×200 ml) the combined organic layers were washed with brine, dried and evaporated to give a white foam (12 g). A crystallisation from a mixture of petroleum and diethyl ether (8/2) (25 ml) afforded the title compound (4.4 g) as a white solid m.p. 145°-147° C.

IR(CDCl$_3$)V$_{max}$ (cm$^{-1}$): 3501(OH), 3414(NH), 1763(C=O), 1713(C=O)

H$^1$-NMR a (CDCl$_3$): 6.29(m), 4.20(m), 4.02(dd), 3.51(d), 2.93(m), 2.81(m), 2.40(m), 2.0-1.8(m), 1.73-1.6(m), 1.03(d), 0.87(s), 0.0(s)ppm.

INTERMEDIATE 8

(3S,4R)-3-[R)-1-(t-butyldimethylsilyloxy)ethyl]-4-[[(R)-1'-(4-methylphenylsulfon)hydrazono]-cyclohex-2'yl]-azetidin-2-one(8a) and (3S,4R)-3-[R)-1-(t-butyldimethylsilyloxy)ethyl]-4-[[(S)-1'-(4-methylphenylsulfon)hydrazono]-cyclohex-2'yl]-azetidin-2-one(8b)

To a solution of example (1K 12.1 g) in glacial acetic acid (120 ml) tosylhydrazide (6.9 g) was added at room temperature. The reaction was stirred for 3 hrs., then diluted with dichloromethane (250 ml) and washed with brine (2×250 ml), then with a 5% solution of sodium hydrogen carbonate until pH 7, and with brine again (2×150 ml). The organic layer was dried and the solvent evaporated under reduced pressure. The obtained foam was stirred with diethyl ether (60 ml) for 2 hrs at room temperature to obtain the title compound 8b as a white powder, after filtration and drying under vacuum (6 g; m.p. 187°-189° C.; t.l.c. diethyl ether Rf=0.13).

IR (CDCl$_3$)V$_{max}$(CM$^1$) 3416(N-H), 3304(NNHSO$_2$), 1753 (lactam), 1559 (C=N; C=C)

H$^1$-NMR (CDCl$_3$): 7.80 (d) 7.38 (bm), 7.34(d), 5.65 (bs), 4.15 (m) 3.58 (dd) 2.63(m), 2.62(m), 2.44(s), 2.3(m), 2.08(m), 1.92(m), 1.78(d), 1.4(m), 1.20(m), 1.185(d), 0.9(s), 0.077(s), 0.067(s).

The organic layer, which contained the title compound 8a in presence of a small amount of the title compound 8b (by t.l.c.), was concentrated and the residue was purified by flash chromatography (eluant dithyl ether/petroleum ether 7:3) to give the title compound 8a as a white powder (7.6 g; m.p. 95°-96° C.; t.l.c. diethyl ether Rf-0.37)

IR (CDCl$_3$)V$_{max}$ (cm$^1$) 3410(N-H), 3306(NNHSO$_2$), 1755(lactam), 1599 (C-N; C=C)

H$^1$-NMR (CDCl$_3$): 7.81(d), 7.40(m), 7.33(d), 5.60(bs) 4.09(m) 4.00(m), 2.81(dd), 2.52(m), 2.44(s), 2.3 (m), 2.0-1.8(m), 1.6-1.4(m), 1.04 (d) 0.87 (s) 0.06 (s), 0.03 (s).

INTERMEDIATE 9

(3S,4R)-3-[R)-1-(t-butyldimethylsilyloxy)ethyl]-4-[[(S)-3'-cyclohex-1'-enyl] azetidin-2-one (3)

A solution of the intermediate (8a 1.12 g) in anhydrous tetrahydrofuran (20 ml) was slowly added, at −40° C., to a stirred solution of diisopropylamine (prepared from anhydrous diisopropylamine (1.35 ml) and a 1.6M solution of n-butyllithium in hexane (5.7)). The reaction was slowly warmed to −20°/0° C. and maintained at −20°/0° C. for 1 h. The reaction mixture was added to a recooled 5% solution of hydrochloric acid (20 ml) and extracted with ethyl acetate (2×40 ml). The organic layer was washed with a 5% solution of sodium hudrogen carbonate (20 ml) and brine (20 ml), then dried over anhydrous sodium sulfate and evaporated. The crude product was purified by flash chromatography (eluant diethyl ether/petroleum ether 1/1) to give the title compound as a white powder (0.45 g, m.p. 104°-06° C.; t.l.c. diethyl ether Rf=0.73)

IR (CDCl$_3$) V$_{max}$ (CM$^1$) 3416(N-H), 1753 (lactam), 1603(C=C)

H$^1$-NMR (CDCl$_3$): 5.82(bs),. 5.81(m), 5.60(dd), 4.14(m), 3.46(dd), 2.85(m), 2.2.4(m), 2.00(m), 185-1.70(m), 1.54(m), 1.27(m) 1.23(d), 0.86(s), 0.064(s), 0.054(s).

INTERMEDIATE 10

(3S,4R)-3-[R)-1-(t-butyldimethylsilyloxy)ethyl]-4-[(1'R,2'S,3'R)-1'2'-epoxycyclohex-3'-yl]-azetidin-2-one A solution of metachloroperbenzoic acid (3.76 g; assay 55%) in dichloromethane (50 ml) was added dropwise, at 0° C., to a solution of the intermediate 9 in methylene chloride (50 ml). The solution was warmed to room temperature and stirred for 3 hrs. The reaction mixture was added to a 10% solution of sodium sulfite (50 ml), the washed with a 5% solution of sodium hydrogen carbonate (2×50 ml) and brine (50 ml). The solution was dried and the solvent was evarporated. The crude product was purified by flash chromatography (eluant ethyl acetate-cyclohexane 3/7) to obtain the title compound as a white powder (1.53 g; m.p. 134°-136° C.; t.l.c. diethyl ether Rf=0.3)

IR (CDCl$_3$) V$_{max}$ (cm$^{-1}$) 3413(N-H), 1757 (Lactam)

H$^1$-NMR CDCl$_3$. 5.85 (bm), 4.22(m), 3.77(dd), 3.16(t), 3.12(m), 3.01(m), 2.00-1.7(m), 1.55(m), 1.4(m), 1.24(d), 1.22(m), 0.87(s), 0.67(s).

INTERMEDIATE 11

(3S,4R)-3-[R)-1-(t-butyldimethylsiloxy)ethyl]-4-[(R)-6'-((S)-2'-azido-1'(R)-hydroxycyclohex-6'-yl)]azetidin-2-one To a solution of the intermediate 10 (1.5 g) in methanol (150 ml) under nitrogen, magnesium sulfate heptahydrate (1.135 g) and sodium azide (0.9 g) were added. The resulting mixture was refluxed overnight, poured into water (150 ml) and extracted with dichloromethane (3×150 ml) dried and evaporated to give the title compound (1.49 g), m.p. 124°-125° C.; t.l.c. cyclohexane/ethyl acetate 3/7(Rf 0.68);

IR:V$_{max}$ (CDCl$_3$) 3600, 3416, 2101, 1755 cm$^1$;

1H-NMR (300 MHZ, CDCl$_3$) 6.02(bs) 4.16(m), 3.78(m), 3.72(m), 3.60(dd), 2.99(m), 2.27(bm), 2.0-1.4(m), 1.24(m), 1.28(d), 0.89(s), 0.098(s), 0.092(s) ppm.

INTERMEDIATE 12

(3S,4R)-3-[(R)-1'(t-Butyldimethylsilyloxy)ethyl]-4-[(1"S,2"R,6"S)-1"-hydroxy-2"cyano-cyclohex-6"-yl]-azetidin-2-one Intermediate 10 (2.4 g) was dissolved into a mixture of dimethylformamide (80 ml) and water (40 ml), potassium cyanide (1 g) was added the mixture was warmed at 60 C. for 8 hours, diluted with ether (150 ml) and washed twice with wter (150 ml). The organic layer was dried and evaporated under reduced pressure to give a crude oil which was purified by flash chromatography on silca gel (eluent ether/ethyl acetate 8/2Rf=0.4) to afford the title compound (1.7 g) as a white solid.

IR(cm$^{-1}$): 3611 (OH), 3416(NH), 1755 (CO);

NMR (ppm): 6.12(bs), 4.18-4.16(m), 3.60(dd), 3.0(dd), 2.94(m), 2.74(bs), 2.0-1.87(m), 1.85-1.6(m), 1.6-15(m), 1.29(d), 0.89(s), 0.09(s).

INTERMEDIATE 13

(3S,4R)-3-[(R)-1'(t-Butyldimethylsilyloxy)ethyl]-4-[(1"R,2"R,6"R)-1'-hydroxy-2"-(allyloxycarbonylaminomethyl)cyclohex-6"-yl]-azetidin-2-one Intermediate 12 (1.7 g) was dissolved in acetic acid (15 ml) and platinum dioxide (40 mgr.) was added, the mixture was hydrogenated (1 atm) for 3.5 hours then filtered on a celite pad and the solvent was evaporated under reduced pressure. The residue was redissolved with dry methylenechloride (80 ml) at 0° C., N-ethylpiperdine (1.8 ml) and allychloroformate (0.55 ml) were added and the resulting mixture was stirred for 16 hrs. The solvent was evaporated under recued pressure to give a crude material which was redissolved with ethyl acetate (100 ml) and washed twice with brine (50 ml). The organic layer was dried and evaporated under reduced pressure to give an oil which was purified by flash chromatography on silica gel (eluants cyclohexane/ethylacetate 60/40 Rf=0.5) to afford the title compound (0.7 g) as a white solid.

IR(cm$^{-1}$): 3454(NH), 3416(NH), 1751(CO), 1720(CO);

NMR (ppm) 6.32(s), 5.9(m), 5.06(t), 4.55(m), 3.78-3.6(m), 3.26(m), 3.07-2.7(m), 1.89)m), 1.83-1.2(m), 1.28(d), 0.88(s), 0.1(s), 0.09(s).

INTERMEDIATE 14

(3S,4R)-3[(R)-1-(t-Butyldimethylsilyloxy)ethyl]-4-((R)-6'-(2'-isopropoxy-1'-oxocyclohex-2'-en-yl))azetidin-2-one (14a) and
(3S,4R)-3[(R)-1-(t-Butyldimethylsilyloxy)ethyl]-4-((S)-6'-(2'-isopropoxy-1'-oxocyclohex-2'-en-yl))azetidin-2-one (14b)

To a mixture of 1M solution of Lithium bis(trimethylsilyl)amide in hexane (486 ml) and anhydrous THF (300 ml), under inert atmosphere and cooled to −78° C., a solution of 2-isopropoxy-2-cyclohexenone (30 g) in anhydrous THF (100 ml), was added dropwise. The temperature was maintained at −78° C. for furher 30', then a solution of (3R, 4R)-4-Acetoxy-3-((R)-t-Butyldimethylsilyloxy)ethyl-2-azetidinone (46.59 g) in anhydrous THF (100 ml) was added dropwise. The reaction was kept at −78° C. for 10 min then poured in to a cold saturated solution of ammonium chloride (300 ml), and extracted with diethyl ether. The organic layer, after washing with a cold 1% solution of hydrochoric acid (150 ml) and with a cold saturated solution of sodium hydrogen carbonate, was dried over sodium sulfate and evaporated under reduced pressure. The yellow oily residue was treated with petroleum ether. After filtration, the title compound 14a was obtained as a white solid (8.4 g); m.p. 130° C. dec.; t.l.c. cyclohexane/ethyl acetate 4/6 Rf 0.21;

IR (Nujol), V$_{max}$ (Cm$^{-1}$): 3233 (NH), 1759(C=O β-lactam), 1680(C=O);

H$^1$-MNR, (CDCl$_3$): 5.92(t), 575(bs), 4.29(m), 4.2(m), 2.99(dd), 2.59(m), 2.52(m), 2.09(m) 1.9(m), 1.27(d), 1.25(d), 1.23(d), 0.86(s), 0.06(s) p.p.m.

The mother liquors were evaporated under reduced pressure and submitted to flash chromatography to obtain the title compound 14b as an oil (9.2 g; t.l.c. cyclohexane/ethyl acetate 4/6 Rf 0.21);

IR (Nujol), V$_{max}$ (cm$^{-1}$) 3425(NH), 1755(C=O β-lactam), 1684 (C=O), 1684(C=O), 1624 (C=C).

H$^1$-NMR, (CDCl$_3$): 6.35(bs), 5.95(m), 4.2(m), 3.6(dd), 2.75(m), 2.5(m), 2.44(m), 2.07(m), 1.7(m), 1.27(d), 1.25(d), 0.86(s), 0.07(s), 0.057(s) ppm.

INTERMEDIATE 15

(3S,4R)-3[(R)-1-(t-Butyldimethylsilyloxy)ethyl]-4-((R)-6'-(2'-isopropoxy-1'-hydroxycyclohex-2'-en-6'-yl))azetidin-2-one To an ice-cold solution of intermediate 14a (5.7) in methanol (100 ml) and water (30 ml), sodium borohydride (560 mg) was added in ten portions in 1.5 hrs. During the additions the pH was maintained between 5 and 7.5 with a 5% solution of hydrochloric acid. At the end dichloromethane (200 ml) and water (100 ml) were added. The organic layer, after washing with water, was dried over sodium sulfate and evaporated under reduced pressure to give the title compound as a white foam (5.5 g).

INTERMEDIATE 16

(3S,4R)-3[(R)-1-(t-Butyldimethylsilyloxy)ethyl]-4-((R)-6'-(2'-cyclopentyloxy-1'-oxocyclohex-2'-en-6'-yl))azetidin-2-one (16a) and
(3S,4R)-3[(R)-1-(t-Butyldimethylsilyloxy)ethyl]-4-((S)-6'-(2'-cyclopentyloxy-1'-oxocyclohex-2'-en-6'-yl))azetidin-2-one (16b)

To a mixture of a 1M solution of Lithium bis(trimethylsilyl)amide in hexane (140 ml) and anhydrous THF (70 ml) under inert atmosphere and cooled to −78°, 2-cyclopentyloxy-2-cyclohexenone (8.5 g) dissolved in anhydrous THF (70 ml), was added. The temperature was kept at −78° for 40 minutes, then a cooled solution of (3R,4R)-4-acetoxy-3-((R)-t-Butyldimethylsilyloxy)ethyl-2-azetidinone (11.25 g) in anhydrous THF (70 ml) was added. The reaction mixture was kept at −78° for 5 minutes then it was poured into a cooled mixture of diethyl ether (225 ml), 10% solution of hydrochloric acid (63 ml), water (180 ml) and a saturated solution of ammonium sulfate (180 ml). The organic layer was washed with 10% solution of hydrochloric acid (2×70 ml) and brine (3×70 ml), dried over sodium sulfate and evaporated under reduced pressure. the residue was chromatographed on silica gel using a mixture of cyclohexane/ethyl acetate 9/1 to 8/2 to obtain an equimolar mixture of the two title compounds 16a and 16b (6.82 g).

The title compound 16a was obtained by crystallization from THF/Petroleum 1/5 (2.1 g, m.p. 111–113; t.l.c. cyclohexane/ethyl acetate 1/1 Rf 0.29)

IR (CDCl$_3$), V $_{max}$(CM$^{-1}$): 3412 (NH); 1757 (C=O beta lactam); 1688 (C=)); 1626 (C=C).

H$^1$-NMR (CDCl$_3$): 5.85(t), 5.67(sa), 4.4(m), 4.3(dd), 4.2(m), 2.98(dd), 2.57(m), 2.50(m), 2.1(m), 1.9(m), 1.5(m), 1.22(d), 0.83(s), 0.05(s).

The mother liquors were evaporated under reduced pressure to give the title compound 16b containing a small amount of the compound 16a (2.45 g; t.l.c. cyclohexane/ethyl acetate 1/1 Rf 0.29)

IR (CDCl$_3$), V$_{max}$(cm$^{-1}$): 3425 (NH), 1757 (C=O β lactam), 1684 (C=O), 1624 (C=C).

H$^1$-NMR (CDCl$_3$) 6.38(sa), 5.87(m), 4.41(m), 4.17(m), 3.60(dd), 2.75(m), 2.49(m), 1.20(m), 1.7-1.6(m), 1.235(d), 0.86(s), 0.068(s), 0.054(s).

INTERMEDIATE 17

2-(t-Butyldimethylsilyloxymethyl)-cyclohexanone 2-hydroxymethyl cyclohexanone (8.8 g) tert-Butyldimethylsilyl-chloride (10 g) and Imidazole (4.6 g) were dissolved in DMF (100 ml) at room temperature.

The resulting mixture was stirred for 2 hours, then poured into petroleum ether (200 ml). The organic layer was washed twice with cold 10% sodium hydrogen carbonate (60 ml), dried, evaporated under reduced pressure and purified by flash chromatography (eluants cyclohexane/ethyl acetate 95/5 Rf=0.7) to obtain the title compound (13.6 g) as a yellow oil.

IR: (V$_{max}$ cm$^{-1}$): 3670 and 1703;

NMR (d ppm): 3.96(dd), 3.555(dd), 2.47(m), 2.4-2.2(m), 2.04(m), 1.89(m), 1.65(m), 1.40(m), 0.87(s), 0.048(s), 0.044(s).

INTERMEDIATE 18

(3S,4R)-3-[(R)-1-(t-Butyldimethylsilyloxy)ethyl]-4-[(2'S,6'R)-2'-methoxy-1'-hydroxycyclohex-6'-yl)]azetidin-2-one To a solution of the intermediate 10a (0.1 g) in methanol (10 ml) p-toluenesulfonic acid monohydrate (10 mg) was added at 0°. The resulting mixture was stirred at 22° for 2 hrs, poured into diethyl ether (30 ml), washed with brine (2×50 ml), dried and evaporated to give the crude title compound as a white powder (70 mg; t.l.c. diethyl ether Rf 0.20);

IR (CDCl$_3$) V$_{max}$ (cm$^{-1}$) 3700, 3609, 3418, 1753;

$^1$H-NMR (300 MHZ, CDCl$_3$) 5.85(bs), 4.18(m), 3.88(bm), 3.64(dd), 3.34(s), 3.30(m), 2.95(m), 1.8(m), 1.8-1.4(m), 1.27(d), 0.88(s), 0.08(s).

INTERMEDIATE 19

(3S,4R)-3-[(R)-1-(t-Butyldimethylsilyloxy)ethyl]-4-[(1'S,2'S,6'R)-2'-methylamino-1'-hydroxycyclohex-6'-yl]-azetidin-2-one To a solution of the intermediate 10 (5 g) in 96% ethanol (150 ml) and water (50 ml) ammonium chloride (1.67 g) and methylamine (40 wt % solution in water; 30 ml) were added. The resulting mixture was refluxed for 15 hrs, then poured into a mixture of dichloromethane (150 ml) and brine (400 ml). The aqueous layer was extracted with dichloromethane (2×120 ml) and the organic layer washed with brine (150 ml), dried over anhydrous sodium sulfate and evaporated to give the title compound as a white foam (5.2 g; t.l.c. CH$_2$Cl$_2$/MeOH/NH$_4$OH 23/7/0.5 Rf 0.75);

IR (CDCl$_3$) V$_{max}$ (cm$^{-1}$)3416, 1753;

$^1$H-MNR (300 MHZ, CDCl$_3$) 6.26(bs), 4.20(m), 3.80(m), 3.72(dd), 3.13(m), 2.67(m), 2.49(s), 2.02(m), 1.7-1.2(m), 1.31(d), 0.91(s), 0.12(s).

INTERMEDIATE 20

(3S,4R)-3-[(R)-1-(t-Butyldimethylsilyloxy)ethyl]-4-[(1'S,2'S,6'R)-2'-allyloxycarbonylmethylamino-1'-hydroxycyclohex-6'-yl)]azetidin-2-one To a solution of the intermediate 19 (5.2 g) in dry dichloromethane (120 ml), under nitrogen at 0°, allyl chloroformate (2.2 ml) and 2,2,6,6-tetramethylpiperidine (3.5 ml) were added. The reaction mixture was stirred for 10 min at 0°, then diluted with dichloromethane (60 ml) and washed with a saturated aq. solution of ammonium chloride (2×100 ml), a 5% solution of sodium hydrogen carbonate (100 ml), brine (100 ml), dried over anhydrous sodium sulfate and evaporated in vacuo. The residue was purified by trituration in diethyl ether (30 ml), to obtain the title compound as a white powder (4.54 g; m.p. 159°-161°; t.l.c. dichloromethane/methanol 9/1 Rf=0.64).

IR: V$_{max}$ (CDCl$_3$) 3414, 1753, 1688 cm$^{-1}$;

$^1$H-NMR (300 MHZ CDCl$_3$) 6.2(bs), 5.9(m), 5.2(m), 4.6(m), 4.2(m), 4.04(m), 3.87(dd), 3.8(m), 3.17(dd), 2.86(s), 2.26(m), 1.8-1.2(m), 1.30(d), 0.89(s), 0.10(s), 0.09(s).

INTERMEDIATE 21

(3S,4R)-1-(t-butyldimethylsilyl)-4-acetoxy-3[(R)-(t-butyldimethylsilyloxy)ethyl]azetidin-2-one To a stirred ice-cold solution of the (3S,4R)-4-acetoxy-3((R)-t-butyldimethysilyloxy)ethyl)-2-azetidinone (112 g) in dichloromethane (800 ml), t-butyldimethylchlorosilane (73 g) and triethylamine (80 ml) were added. The mixture was stirred at room temperature for 20 hours then washed with water (1 l) and brine (300 ml). The organic layer was dried and evaporated to give an oil (160 g) which was dissolved in a mixture of cycloexane/ethyl acetate (95/5) (1600 ml) and treated with silica gel (480 g). The suspension was stirred for 15 min then filtered. The solid was washed with cyclohexane/ethyl acetate (95/5:4.81) and the solvent evaporated to give the title compound (110 g) as a pale yellow oil. (Rf =0.85 Petrol/Diethyl ether=2/1)

IR(CDCl$_3$)V$_{max}$ (cm$^{-1}$): 1747(C=O)

H$^1$-NMR a (CDCl$_3$):6.14(d), 4.15(m), 3.07(dd), 2.03(s), 1.2(d), 0.9(s), 0.84(s), 0.22(s), 0.055(s), 0.35(s), 0.005(s)ppm.

INTERMEDIATE 22

(3S,4R)-1-(t-butyldimethylsilyl)-3-[(R)-1-(t-butyldimethylsilyloxy)ethyl]-4-[2'-(1'-oxo-cyclohexyl]azetidin-2-one Stannic chloride (35.4 ml) was added dropwise to stirred acetonitrile (400 ml) under nitrogen atmosphere at −40° C., a white solid formed together with white fumes which were eliminated by nitrogen flushing. The obtained suspension was allowed to rise to −10° C. then a solution of 1-trimethylsilyloxycyclohexene (60.6 ml) and compound of Intermediate 21 (110 g) in acetonitrile (300 ml) was added in 10 minutes. The yellow solution was stirred at 0° C. for 10 min then poured into a stirred, ice-cold, mixture of a 10% aq solution of sodium hydroxide (1 l), diethyl ether (1 l) and ice (500 g). The organic layer was separated, washed again with sodium hydroxide (500 ml) and then with a saturated solution of ammonium chloride, dried and evaporated to give a yellow solid (117.7 g). The solid was dissolved at 40° C. in isopropanol (300 ml) then cooled at room temperature, water (300 ml) was added slowly under stirring to obtain a solid which was stirred at 0° C. for 30 min then filtered, washed with a 1 to 1 mixture of isopropanol/water (100 ml) and dried under vacuum at 40° C. for 15 hourse to afford the title compound (76 g) as a mixture of 2'R and 2'S isomers in a ratio of 70% to 30% (the ratio between the two isomers was determinated by HPLC using exane/ethanol (99/1) as eluant).

INTERMEDIATE 23

(3S,4R)-1-(t-butyldimethylsilyl)-3-[(R)-1-(t-butyldimethylsilyloxy)ethyl]-4-[6'-(1'-trimethylsilyloxycyclohex-1'-enyl)]azetidin-2-one A 1M solution of lithium bis(trimethylsilyl)amide in hexane (70 ml) was added to tetrahydrofurane (150 ml), the mixture stirred under nitrogen, cooled to −70° C. and then a solution of the compound of Intermediate 22 (15.5 g) in tetrahydroduran (70 ml) was added over 20 min. The obtained solution was stirred for 30 min then chlorotrimethylsilane (10 ml) was added over 10 min. The reaction temperature was allowed to rise to −20° C. then the mixture was poured into a saturated ammonium chloride solution (500 ml) and the resulting mixture extracted with diethyl ether (300 ml). The organic layer was washed with water (200 ml), a 2% ice-cold solution of hydrochloric acid (300 ml), aqueous solution of sodium hydrogen carbonate and brine, dried and evaporated under reduced pressure to give the title compound as a crude mixture of 6'R and 6'S isomers.

INTERMEDIATE 24

2-(2-benzyloxyethoxy)-cyclohexanone

A mixture of dimeric 2-hydroxycyclohexanone (13.7 g), 2-benzyloxyethanol (20 g) and p-toluensulphonic acid (2 g) were dissolved in xylene (500 ml) in a round bottom flask fitted with a Dean Stark apparatus and reluxed for 10 hrs. The resulting solution was cooled, washed with sodium hydrogen carbonate (3×50 ml) dried and concentrated under reduced pressure. The crude oil was then pruified by flash chromatography using cyclohexane/ethyl acetate 60/40 as eluant yielding 20 g of the title compound (RF=0.5).

IR, CDCl$_3$, (cm$^{-1}$): 1722 (C=O), 1603(C=C).

$^1$H-MNR, 300 MHz, CDCl$_3$, chemical shift (ppm, TMS): 7.32(m), 4.55(dd), 3.92(m), 3.83(m), 3.64(m), 3.60(m), 2.48(m), 2.24(m), 1.93(m), 1.8-1.55(m).

EXAMPLE 1

(3S,4R)-3-[(R)-1-(t-Butyldimethylsilyloxy)ethyl]-4-((R)-2'-(1'-oxocyclohexyl)]azetidin-2-one (1a) and (3S,4R)-3-[(R)-1-(t-Butyldimethylsilyloxy)ethyl]-4-((S)-2'-(1'-oxocyclohexyl)]azetidin-2-one (1b)

Method A

1-Trimethylsilyloxycyclohexene (11 g) was dissolved in methylene chloride (400 ml) under nitrogen. (3R,4R)-4-Acetoxy-3((R)-(t-butyldimethylsilyloxy)ethyl)-2-azetidinone (9.28 g; intermediate A) was added to the solution, the mixture stirred at 23° and trimethylsilyl trifluoromethanesulphonate (0.66 g) was added. The mixture was stirred under nitrogen for 2 hr and then poured into an ice cold 1% solution of sodium hydrogen carbonate (300 ml). The organic layer was separated, washed with water (300 ml) and brine (300 ml). The oily residue obtained, after evaporating the solvent under reduced pressure was chromatographed (gradient elution with EE/P) to give the title compound (1a; 2.6 g) as a white solid m.p. 70°-80° (t.l.c. P/EA 4/6; Rf 0.5) and the title compound (1b; 2.63 g) as a white solid m.p. 100° (t.l.c. P/EA 4/6; Rf 0.45).

Method B

A 1M solution of lithium bis(trimethylsilyl)amide in hexane (250 ml) was added to tetrahydrofuran (250 ml), the mixture stirred under nitrogen, cooled to −78° and cyclohexanone (15.2 g) was added over 20 min. The temperature was allowed to rise to −55° for 10 min and then the mixture cooled to −78° for 40 min. Intermediate A (34 g) was added and the resulting mixture stirred for 30 min at −78°. The reaction mixture was poured into a saturated ammonium chloride solution (200 ml) and the resulting mixture extracted with ethyl acetate (3×200 ml). The combined organic layers were washed with brine, dried and evaporated under reduced pressure. The oily residue was chromatographed (gradient elution with CH/EA) to give the title compound (1a; 11.6 g) as a white solid m.p. 70-80 and the title compound (1b; 12 g) as a white solid m.p. 100° C.

Using Method A (3S,4R)-3-[(R)-1-(t-butyldimethylsilyloxy)ethyl]-4((S)-6'-(1'-oxocyclohex-2'-enyl)-azetidin-2-one (1c; 12.7 g), m.p. 125° was prepared from 2-trimethylsilyloxycyclohex-1,3-diene (19.2 g) and intermediate A (14.34 g) except that the reaction time was 18 hr and the crystalline product was obtained from the oily residue by crystallisation from EE/P in place of the chromatographic purification step.

Using method B—

(3S,4R)-3-[(R)-1-(t-butyldimethylsilyloxy)ethyl]-4-((S)-2'-((R)-6'-methyl-1'-oxocyclohexyl))azetidin-2-one (1d; 0.5 g) m.p. 117° and a mixture (example 1e; 3.15 g) of (3R,4R)-3-[(R)-1-(t-butyldimethylsilyloxy)ethyl]-4-((S)-2'((S)-6'-methyl-1'-oxocyclohexyl))azetidin-2-one and (3R,4R)-3-[(R)-1-(t-butyldimethylsilyloxy)ethyl]-4-((R)-2'-((S)-6'-methyl-1'-oxocyclohexyl))azetidin-2-one were prepared from intermediate A (14.35 g) and 2-methyl-1-oxo-cyclohexane 13.2 g.

(3S,4R)-3-[(R)-1-(t-Butyldimethylsilyloxy)ethyl]-4-((S)-2'-(6',6'-dimethoxy-1'-cyclohexyl))azetidin-2-one (1f; 0.97 g) from intermediate A (1.8 g) and 2,2-dimethoxy-1-oxocyclohexane (2.0 g) except that the chromatography eluants were EE and P.

(3S,4R)-3-[(R)-1-(t-Butyldimethylsilyloxy)ethyl]-4-((R)-6'-(2'-methoxy-1'-oxocyclohex-2'-enyl))]azetidin-2-one (1 g) and (3S,4R)-3-[(R)-1-(t-Butyldimethylsilyloxy)ethyl]-4-((S)-6'-(2'-methoxy-1'-oxocyclohex-2'-enyl))]azetidin-2-one (1 h)

2-Methoxy-2-cyclohexenone (11.9 g) was added dropwise to a stirred mixture of anhydrous tetrahydrofuran (200 ml) and a 1M solution of lithium bis(trimethylsilyl)amide in hexane (200 ml) cooled to −78° and under nitrogen. The temperature was maintained at −78° for a further 30 min, intermediate A (15 g) added and the reaction mixture kept at −78° for an additional 15 min. The reaction mixture was poured into a cold saturated solution of ammonium chloride (100 ml) and then extracted with ether. The organic layer was washed with a cold 1% solution of hydrochloric acid (50 ml) and a cold saturated solution of sodium hydrogen carbonate, dried and then evaporated under reduced pressure. The residue was dissolved in the minimum amount of ethyl acetate and petroleum ether (200 ml) added to give the title compound (1h; 7.9 g) as a white solid m.p. 170° (t.l.c. Rf 0.25; CH/EA 4/6). The mother liquors were evaporated under reduced pressure and submitted to flash chromatography to give the title compound (1g; 2.9 g) (t.l.c. Rf 0.20; CH/EA 4/6).

(3S,4R)-3-[(R)-1-(t-Butyldimethylsilyloxy)ethyl]-4-((R)-6'-(2'-ethoxy-1'-oxocyclohex-2'-enyl))]azetidin-2-one (1i) and
(3S,4R)-3-[(R)-1-(t-Butyldimethylsilyloxy)ethyl]-4((S)-6'-(2'-ethoxy-1'-oxocyclohex-2'-enyl)]azetidin-2-one (1j)

A solution of 2-ethoxy-2-cyclohexenone (24 g) in anhydrous tetrahydrofuran was added to a mixture of anhydrous tetrahydrofuran (160 ml) and a 1M solution of lithium bis(trimethylsilyl)amide in hexane (200 ml) cooled to −78° and under nitrogen and with the resultant mixture kept at −78° for 1 h. A solution of intermediate A (26.3 g) in tetrahydrofuran (80 ml) was then added over 10 min. A cold saturated solution of ammonium chloride (320 ml) was added followed by a 10% solution of hydrochloric acid (70 ml). The resultant mixture was extracted with ether (3×150 ml) washed with cold 10% hydrochloric acid (50 ml), brine and then dried. Removal of the solvent under reduced pressure gave an oily residue which was purified by flash chromatography (eluants CH/EA) to give a 1:1 mixture of the title compounds (20 g) and pure title compound (1j; 1.3 g) (t.l.c. Rf 0.36; CH/EA 1/1). The mixture was dissolved in the minimum amount of ethyl acetate, diluted with cyclohexane and chilled to give the title compound (1i; 4 g) as a white solid (t.l.c. Rf 0.38; CH/EA 1/1).

EXAMPLE 1 K (3S,4R)-3-[(R)-1-(t-Butyldimethylsilyloxy)ethyl]-4-((R)-2'-(1'-oxocyclohexyl)]azetidin-2-one and
(3S,4R)-3-[(R)-1-(t-Butyldimethylsilyloxy)ethyl]-4-((S)-2'-(1'-oxocyclohexyl)]azetidin-2-one 1-Trimethylsilyloxycyclohexene (11 g) was dissolved in methylene chloride (400 ml) under nitrogen. (3R,4R)-4-Acetoxy-3((R)-(t-butyldimethylsilyloxy)ethyl)-2-azetidinone (9.28 g; intermediate A) was added to the solution, the mixture stirred at 23° and trimethylsilyl trifluoromethanesulphonate (0.66 g) was added. The mixture was stirred under nitrogen for 2 hr and then poured into an ice cold 1% solution of sodium hydrogen carbonate (300 ml). The organic layer was separated, washed with water (300 ml) and brine (300 ml). Evaporation of the solvent under reduced pressure gave a mixture of the title compounds as an oil.

EXAMPLE 2

(3S,4R)-3-[(R)-1-(t-Butyldimethylsilyloxy)ethyl]-4((R)-2'-((S)-6'-methoxy-1'-oxocyclohexyl))]azetidin-2-one (2a) and
(3S,4R)-3-[(R)-1-(t-Butyldimethylsilyloxy)ethyl]-4((R)-2'((R)-6'-methoxy-1'-oxocyclohexyl))]azetidin-2-one (2b)

10% Palladium on charcoal (1.8 g) was added to a solution of example (1 g: 2.2 g) in ethyl acetate (200 ml) and the mixture was hydrogenated at 1 atmosphere for 2 hr. The catalyst was removed by filtration and the filtrate evaporated under reduced pressure. The oily residue was chromatographed (eluants EA/CH 9/1) to give the title compound 2a (0.6 g) (t.l.c. Rf 0.8; EA/CH 9/1) as a light yellow oil. Further elution gave the title compound 2b (1.1 g) (t.l.c. Rf 0.4; EA/CH 9/1) as an oil.

In a similar manner:

(3S,4R)-3-[(R)-1-(t-Butyldimethylsilyloxy)ethyl]-4-((S)-2'-((S)-6'-methoxy-1'-oxocyclohexyl))]azetidin-2-one (2c; 2.1 g) was obtained from example 1h (2.2 g);
(3S,4R)-3-[(R)-1-(t-Butyldimethyisilyloxy)ethyl)-4((R)-2'-((S)-6'-ethoxy-1'-oxocyclohexyl))]azetidin-2-one (2d; 0.95 g) (t.l.c. Rf 0.57; eluants EA/CH 1/1) and
(3S,4R)-3-[(R)-1-(t-Butyldimethylsilyloxy)ethyl]-4-((R)-2'-((R)-6'-ethoxy-1-oxocyclohexyl))]azetidin-2-one (2e; 3 g) (t.l.c. Rf 0.35 eluants EA/CH 1/1) from example 1i (4.4 g).

EXAMPLE 3

(3S,4R)-3-[(R)-1-(t-butyldimethylsilyoxy)ethyl]-4-((R)-2'-((S)-6'-methylthio-1'-oxocyclohexyl))azetidin-2-one
3a 2-Mercaptopyridine (1.63 g) and triethylamine (1.49 g) were added to a solution of intermediate 2 (5.60 g) in methylene chloride under nitrogen and cooled at 0°. The reaction mixture was stirred at 23° for 2 hrs and then poured into cold 2% hydrochloric acid (200 ml). The organic layer was separated, washed with dilute hydrochloric acid (2×200 ml) and then with water (2×200 ml). The residue obtained after evaporating the solvent was purified by flash chromatography (eluants EE/P) to give the title compound 3a (3.87 g) as a light yellow oil.
$H^1$ NMR (CDCl$_3$) ppm. $H_3$ 2.88(dd), $H_4$ 4.16(m).

In a similar manner (3S,4R)-3-((R)-1-(t-Butyldimethylsilyloxy)ethyl-4-((S)-2'-((S)-6'-methylthio-1'-oxocyclohexyl))azetidine-2-one (3b; 0.6 g) $H^1$NMR (CDCl$_3$) ppm. $H_3$ 2.70 (m) $H_4$ 3.68 (dd) was prepared from Intermediate 3b (0.84 g), and (3S,4R)-3-[(R)-1-(t-Butyldimethylsilyloxy)ethyl]-4-((S)-2'-((R)-6'-methylthio-1'-oxocyclohexyl))azetidin-2-one (3c; 0.5 g) $H^1$NMR (CDCl$_3$) ppm $H_3$ 2.73(m), $H_4$ 3.59(dd) was prepared from Intermediate 3a (0.7 g).

EXAMPLE 4

(3S,4R)-3-[(R)-1-(t-butyldimethylsilyloxy)ethyl]-4-[(R)-2'-(S)6'-trimethylsilyloxy-1'-oxocyclohexyl]azetidin-2-one The compound of Intermediate 7 (4.4 g) was dissolved in dry dichloromethane (100 ml) at room temperature. Trimethylsilyl chloride (7.5 ml) followed by triethylamine (11 ml) were added and the mixture was stirred for 1 h, then poured into water (200 ml). The organic layer was separated and washed with water (2×200 ml), dried and evaporated to give a yellow oil containing traces of TEA. The oil was dissolved in methanol (100 ml), trated with silica gel (10 g) and the suspension was stirred for 1 h then filtered. The silica gel was washed with ethyl acetate (2×100 ml) and the combined organic layers evaporated under reduced pressure at 25° C. The obtained oil was dissolved with ethyl acetate (150 ml), washed with brine, dried and evaporated to give a yellow foam which wash chromatographed on silica gel using a mixture of petroleum and diethyl ether (1/1) as eluant (Rf) 0.25) to afford the title compound (3.5 g) as a white foam.
IR(CDCl$_3$) V$_{max}$ (cm$^{-1}$): 3418(NH), 1755(C=O) 1717(C=O)
H$^1$-NMR a (CDCl$_3$): 5.77(s), 4.16(m), 4.01(m), 3.95(m), 3.20(m), 2.86(dd), 2.1(m), 1.4(m), 1.25(d), 0.86(s), 0.10(s), 0.07(s), 0.05(s)ppm.

EXAMPLE 5

(3S,4R)-3-[(R)-1-(t-butyldimethylsilyloxy)ethyl]-4-[(R)-6'-((S)-2'-azido-1'-oxocylohex-6'-yl)]azetidin-2-one To a mixture of pyridinium chlorochromate (6.67 g) in dry dichloromethane (50 ml), under nitrogen, a solution of the intermediate 11 in dichloromethane (200 ml) was added. The mixture was stirred at room temperature overnight, filtered through florisil and the resulting solution evaporated under reduced pressure. The oily residue was chromatographed on silica gel using a cyclohexane/ethylacetate (1/1) mixture as eluant to afford the title compound (4 g; m.p. 134°-135° C. dec; t.l.c. diethyl ether Rf 0.68);

IR:$V_{max}$ (CDCl$_3$)3416, 2104, 1759, 1720 cm$^1$;

$^1$H-NMR (300 MHZ. CDCl$_3$) 5.77 (bs), 0.2(m), 4.04(m), 3.00(m), 2.9(m), 2.15-1.3(m), 1.21(d), 0.87(s), 0.074(s), 0.065(s)ppm.

EXAMPLE 6

(3S,4R)-3-[(R)-1-(t-butyldimethylsilyloxy)ethyl]-4-[(R)-6'-((S)-2'-allyloxycarbonylamino-1'oxocyclohex-6'yl)-]azetidin-2-one The Example 5 (4 g) was dissolved in ethyl acetate (300 ml), 10% palladium on charcoal (3 g) added and the mixture hydrogenated at 3 atm for 2 hrs. A further amount of the catalyst (1 g) was added and the hydrogenation was continued for 2 hrs. The mixture was filtered through a pad of celite and the resulting solution treated with allychloroformate (1.7 g) and pyridine (1.12 g). The reaction mixture was kept under stirring for 30 min at room temperature, then poured into a saturated aq. solution of ammonium chloride (350 ml). The organic layer was washed with a 1% solution of hydrochloric acid (2×150 ml), then with a 5% solution of sodium hydrogen carbonate (2×150 ml) and brine (200 ml), dried and evaporated in vacuo. The residue was purified by flash chromatography on a silica column, using a cyclohexane-ethyl acetate (1/1) mixture to obtain the title compound as an oil (2 g; t.l.c. cyclohexane/ethyl acetate 3/7 Rf=0.4).

IR: $V_{max}$(CDCl$_3$) 3414, 1765, 1709 cm$^1$;

$^1$H-NMR (300 MHZ, CDCl$_3$) 6.05(s), 5.9(m) 5.64(bd), 5.26(m), 4.56(m), 4.4-41(m), 4.05(dd), 2.9(m), 2.75(m), 2.60(m), 2.0-1.2(m), 1.02(d), 0.86(s), 0.06(s).

EXAMPLE 7

(3S,4R)-3-[(R)-1'(t-Butyldimethylsilyloxy)ethyl]-4-[2"R,6"R)-1"'-oxo-2"'-(allyloxycarbonylaminomethyl)-cyclohex-6"-yl)]azetidine-2-one Intermediate 13 (0.7 g) was dissolved in methylene chloride (50 ml) and pyridinium chlorochromate (1.1 g) was added under vigorous stirring. After 2.5 hours the mixture was filtered on a celite pad diluted with methylene chloride (150 ml) was washed with cold 5% hydrochloric acid (20 ml) then with sodium hydrogencarbonate (20 ml). The organic layer was dried and evaporated under reduced pressure to give an oil which was purified by flash chromatography on silica gel (eluants cyclohexane ethylacetate 30/70 Rf=0.3) to afford the title compound (0.48 g) as a white sold.

IR $V_{max}$ cm$^{-1}$): 3456 and 3439 (NH), 1759 (CO), 1720 and 1718 (CO), 1603(C=C);

NMR (d ppm) 6.02(bs), 5.98 (m), 5.23(m), 5.12(bt), 4.5(m), 4.21(m), 4.05(m), 13.35(m), 2.92(bs), 2.68(m), 2.58(m), 2.1-1.55(m), 1.32-1.2(m), 1.04(d), 0.87(s), 0.06(s).

EXAMPLE 8

(3S,4R)-3[(R)-1-(t-Butyldimethylsilyloxy)ethyl]-4-[((R)-2'-((S)-6'-isopropoxy-1'-oxocyclohexyl))]azetidin-2-one (8a)

(3S,4R)-3[(R)-1-(t-Butyldimethylsilyloxy)ethyl]-4-[((R)-2'-((R)-6'-isopropoxy-1'-oxocyclohexyl))]azetidin-2-one (8b)

The intermediate 15 (5.5 g) was dissolved in ethanol (100 ml). Then 10% palladium on charcoal (0.5 g) was added and the mixture was hydrogenated at 3 atm for 4 hrs. The catalyst was filtered off and the solution was evaporated under reduced pressure. The oily residue (5 g) was dissolved in anhydrous dichloromethane (150 ml) and pyridinium chlorochromate (4.2 g) was added. The reaction mixture was stirred at 20° C. for 6 hrs, then more pyridinium chlorochromate (2.8 g) was added. The reaction was stirred for further 4 hrs. then diluted with diethyl ether (100 ml) and decanted from black gum, which was washed twice with diethyl ether. The organic solutions were combined and evaporated under reduced pressure; the oily residue was chromatographed using a mixure ethyl acetate/cyclohexane 9/1) to obtain the title compound 8a as a white solid (0.8 g; t.l.c. ethyl acetate/cyclohexane 1/1 Rf 0.5);

IR(CDCl$_3$), $V_{max}$ (cm$^{-1}$): 3416(NH), 1755(C=) β lactam), 1705(C=O ketone).

H$^1$-NMR(CDCl$_3$): 5.89(bs), 4.17(m), 3.97(m), 3.78(m), 3.53(m), 3.15(m), 2.86(dd), 2.13(m), 2.10(m), 1.8-1.4(m), 1.24(d), 1.13(d), 0.88(s), 0.08(s), 0.06(s)ppm.

Further elution gave the title compound 8b as a white solid (1g; m.p. 121° C.; t.l.c. ethyl acetate/cyclohexane 1/1 Rf 0.28);

IR(CDCl$_3$), $V_{max}$ (Cm$^{-1}$): 3416(NH), 1759(C=O β lactam), 1722(C=O).

H$^1$NMR(CDCl$_3$): 5.7(bs), 4.18(m), 4.09(m), 3.97(dd), 3.6(m), 2.8(dd) 2.55(m), 2.3(m), 2.1(m), 1.98(m), 1.8-1.6(m), 1.22(d), 1.14(d), 0.8(s), 0.07(s), 0.06(s) ppm.

EXAMPLE 9

(3S,4R)-3[(R)-1-(t-Butyldimethylsilyloxy)ethyl]-4-[((2'R,6,'S)-2'-cyclopentyloxy-1'-oxocyclohex-6'-yl))azetidin-2-one The intermediate 16b (3.2 g) was dissolved in ethyl acetate (290 ml) 10% Palladium on charcoal (1.35 g) was added and the mixture was hydrogenated at 3 atm for 1 hr. The catalyst was filtered off through a pad of celite, and the solution was evaporated under reduced pressure. The residue was chromatographed on silica gel, using a mixture of ethyl acetate/cyclohexane 9/1 to 7/3 to obtain the title compound as a white foam (1.2 g); t.l.c. cyclohexne/ethyl acetate 1/1 Rf 0.45)

IR (CDCl$_3$), $V_{max}$(cm$^{-1}$): 3418 (NH), 1755 (C=O β lactam), 1722(C=O).

H$^1$-NMR (CDCl$_3$): 6.097(sa), 4.15(m), 4.01(m), 3.905(m), 3.67(dd), 2.69(m), 2.43-2.22(m), 2.10(m), 2.00-1.90(m), 1.83-1.50(m), 1.33(m), 1.22(d), 0.86(s), 0.075(s), 0.049(s).

EXAMPLE 10

(3S,4R)-3-[(R)-1-(t-Butyldimethylsilyloxy)ethyl]-4-[(2"R,6"R)-2"(t-Butyldimethysilyloxymethyl)-1"-oxocyclohex-6"-yl] azetidin-2-one and
(3S,4R)-3-[(R)-1-(t-Butyldimethylsilyloxy)ethyl]-4-[(2"S,6"R)-2"(t-Butyldimethsilyloxymethyl)-1"-oxocyclohex-6"-yl] azetidin-2-one 2,2,6,6-Tetramethyl piperidine (28.3 ml) was added dropwise to a stirred solution of butyl lithium 1.6M in hexane (125 ml) in dry THF (150 ml) under nitrogen and cooled at −50°. The resulting mixture was warmed at 5° C. for 10 min cooled at −78° C., and intermediate 17 (23 g) in dry THF (100 ml) was added dropwise at −70° C. After 1 hour, (3R,4R)-4-Acetoxy-3-((R)-(tert-butyldimethylsilyloxy)ethyl-2-acetidinone (27.5 g) was added and the resulting mixture was stirred for 40 min at −78° C. The reaction mixture was poured into a saturated solution of ammonium chloride (300 ml), extracted twice with ethyl acetate (250 ml), the organic layer was dried and evaporated under reduced pressure. The oil obtained was purified by flash chromatography (eluants cyclohexane/ethyl acetate 90/10 Rf=0.3) to give a mixture of the title compound (17 g) as a yellow solid.

IR: ($V_{max}$ cm$^1$) 3582, 1755(CO β-lactam), 1612
NMR: (d ppm): 6.1-5.7 (bs+bs+bs). 4.18(m), 4.06(m), 3.97(m), 3.90(m), 3.51(m), 3.74(m), 2.86(m), 2.7-2.5(m), 2.40(m), 2.14(m), 2.1-1.6(m), 1.32(m), 1.24(d), 1.17(d), 0.87(s+s+s), 0.05(m).

EXAMPLE 11

(3S,4R)-3-[(R)-1-(t-Butyldimethylsilyloxy)ethyl]-4-((2'S)-((6'R,S)-6'-iodo-1'-oxocyclohex-2-yl]azetidin-2-one To a stirred 1M solution of LHMDA* in hexanes (48.7 ml), dissolved in anhydrous THF (70 ml) cooled to −78 C. under nitrogen atmosphere a solution of example 1a (7.2 g) in THF (70 ml) was added. The resulting mixture was stirred at −70 for 1.5 hrs, cooled to −78 C. and a solution of iodine (7.4 g) in anhydrous THF (20 ml) was slowly added. The reaction was stirred for further 10 min then brine (250 ml) was added at −78 C. The resulting mixture was extracted twice with ether (150 ml); the organic layer was washed twice with a saturated solution of sodium sulphite (100 ml) and with water (100 ml). The organic layer was dried over sodium sulphate, evaporated under reduced pressure and the crude material (9.5 g) was used without any further purification.

*(LHMDA designates lithium bis(trimethylsilyl)amide)

EXAMPLE 12

(3S,4R)-3-[(R)-1-(t-Butyldimethylsilyloxy)ethyl]-4-((2'S)-2'((6'S)-6'-phenylthio-1'-oxocyclohex-2'-yl)]azetidin-2-one 12a
(3S,4R)-3-[(R)-1-(t-Butyldimethylsilyloxy)ethyl]-4-((2'S)-2'((6'R)-6'-phenylthio-1'-oxocyclohex-2'-yl)]azetidin-2-one 12b Thiophenol (7.424 g) was dissolved into a solution of potassium hydroxide (5.33 g) in water (740 ml) under stirring. To the resulting solution tetrabutyl ammonium bromide (1.52 g) was added followed by a solution of example 11(15.2 g) in methylene chloride (500 ml). The resulting mixture was stirred for 16 hrs. The organic layer was separated and the aqueous phase was extracted with methylene chloride. The organic layer was dried over sodium sulphate and evaporated under reduced pressure. The residue was chromatgraphed (elutants cyclohexane/ethyl acetate 7/3) to give thiophenol (4.9 g) and a mixture (5.34 g) of the title compounds 12a and 12b and example 1A. The mixture was chromatographed using petroleum ether 40–60/diethyl ether 9/1 as elutant to give title compound 12a (0.1 g) as the first eluted material and a mixture of title compounds 12a and 12b (1.1 g) as the second eluted material. The second eluted material was further purified by HPLC (silica, n-hexane/ethyl acetate 8/2, 10 ml/min, uv detection set at 275) to give the title compound 12a (0.7 g) as a white solid (m.p. 116-7 from cyclohexane) and title compound 12b (0.12 g) as a light yellow solid m.p. 65°-7°.

Title Compound 12a $^1$H-NMR (ppm) 7.4-7.2(m), 5.8 (bs); 4.13(m); 3.9(m); 3.8(m); 3.46(m); 2.75 (dd); 2.3(m); 2.2(m); 2.00(m); 1.8(m); 1.6(m); 1.18(d); 0.8(s); 0.019(s).

Title compound 12b $^1$H-NMR (ppm) 7.4-7.3(m); 5.77(bs); 4.17(m); 4.11(m); 3.95(m); 2.8(dd); 2.6(m); 2.4(m); 2.2(m); 2.00(m); 1.7(m); 1.4(m); 1.23(d); 0.86(s); 0.06(s); 0.055(s).

EXAMPLE 13

(3S,4R)-3-[(R)-1-(t-Butyldimethylsilyloxy)ethyl]-4-[(2'S,6'R)-2'-methoxy-1'-oxocyclohex-6'-yl)]azetidin-2-one To a solution of the intermediate 18 (70 mg) in dry dichloromethane (8 ml) a mixture of pyridiniumchlorochromate (80 ml) in dry dichloromethane was added, under nitrogen. The resulting mixture was stirred at 22° for 4 hrs, then diluted with diethyl ether (30 mg), decanted from black gum and filtered through florisil. The organic solution was evaporated under reduced pressure to give the title compound as a pale yellow powder (30 mg; t.l.c. cyclohexane/ethyl acetate 4/6 Rf 0.43);

IR (CDCl$_3$), $V_{max}$ (cm$^{-1}$): 3418, 1757, 1718;
$^1$H-NMR (300 MHZ, CDECl$_3$) 5.84(sa), 4.18(m), 3.99(m), 3.57(m), 3.28(s), 3.10(m), 2.876(dd), 2.24(m), 2.08(m), 1.98(m), 1.68(m), 1.56(m), 1.248(d), 0.87(s), 0.075(s), 0.063(s).

EXAMPLE 14

(3S,4R)-3-[(R)-1-(t-Butyldimethylsilyloxy)ethyl]-4-[(2'S,6'R)-2'-(N-allyloxycarbonyl-N-methylamino)-1-'-oxocyclohex-6'-yl)]azetindin-2-one

Method A

To a solution of the intermediate 20 (1.8 g) in dry dichloromethane (50 ml) pyridiniumchlorochromate (2.2 g) was added under nitrogen. The reaction mixture was stirred at 22° for 5 hrs, then filtered through florisil, washing with ethylacetate (200 ml), and the resulting solution evaporated under pressure. The oily residue was chromatographed on silica gel, using a cyclohexane/ethylacetate 1/1 mixture as elutant to, afford the title compound as a white powder (1.0 g; m.p. 140°-142°).

Method B

To a solution of oxalyl chloride (3.35 ml) in dry dichloromethan (15 ml), under nitrogen at −70°, a solution of dimethyl sulfoxide (3.35 ml) in dry dichloromethane (40 ml) was added dropwise in 15 min. After 15 min, a solution of the intermediate 20 (4.34 g) in dry dichloromethane (35 ml) was added dropwise in 20 min and the solution was stirred at −70° for 2 hr, then triethylamine (14 ml) was added with warming to −40° in 10 min. The solution was washed with a saturated solution of ammonium chloride (2×100 ml), brine (2×100 ml), dried over anhydrous sodium sulfate and evaporated. The crude product was triturated with a mixture of petroleum ether (40 ml) and diethyl ether (10 ml) to give the title compound as a white powder (3.71 g; m.p. 140°-142°; t.l.c. diethyl ether Rf 0.3;);

IR: $V_{max}$ (CDCl$_3$) 3414, 1763, 1718, 1691 cm$^{-1}$;

$^1$-H-NMR (300 MHZ, CDCl$_3$) 6.08(bs), 5.92(m), 5.3-5.1(m), 4.55(m), 4.20(m), 4.03(dd), 2.99(m), 2.85(s), 2.66(m), 2.08-1.8(m), 1.06(bd), 0.86(s), 0.06(s) ppm.

EXAMPLE 15

(3S,4R)-3-[(R)-1(t-butyldimethylsilyloxy)ethyl]-4-[(R)[2'-(S)-6'-hydroxy-1'-oxocyclohexyl]azetidin-2-one The compound of Intermediate 23 was dissolved at −10° C. in dichloromethane (300 ml) and treated with sodium hydrogen carbonate (2.85 g). To the obtained suspension, 3-chloroperoxybenzoic acid (8.5 g) was added portionwise over 30 min. The reaction mixture was stirred at 0° C. for 1.5 h and at room temperature for 1 h then solid sodium sulphite (5 g) was added. After stirring for 30 min the solid was filtered and washed with dichloromethane (100 ml). The organic layer was washed with a 3% aqueous sodium sulphite solution (100 ml) followed by an ice-cold 3% aqueous sodium hydrogen carbonate solution (3×150 ml) and water, dried and evaporated to give a yellow oil which was dissolved in methanol (250 ml). Potassium fluoride (6 g) was added and the obtained solution stirred at room temperature for 30 min then poured into a saturated solution of ammonium chloride (500 ml) and the resulting mixture extracted with ethyl acetate (3×200 ml) the combined organic layers were washed with brine, dried and evaporated to give a white foam (12 g). A crystallisation from a mixture of petroleum and diethyl ether (8/2) (25 ml) afforded the title compound (4.4 g) as a white solid m.p. 145°-147° C.

IR(CDCl$_3$)V$_{max}$ (cm$^{-1}$): 3501(OH), 3414(NH), 1763(C=O), 1713(C=O)

H$^1$-NMR a (CDCl$_3$): 6.29(m), 4.20(m), 4.02(dd), 3.51(d), 2.93(m), 2.81(m), 2.40(m), 2.0-1.8(m), 1.73-1.6(m), 1.03(d), 0.87(s), 0.0(s)ppm.

EXAMPLE 16

(3S,4R)3-[(R)-1-(t-butyldimethylsilyloxy)ethyl]-4-[(R)2'-[(S)6'-(2benzyloxyethoxy)-1'-oxocyclohexyl]-]azetidin-2-one 2,2,6,6-tetramethylpiperidine (12.7 g) was dropped to a solution of n-butyllithium 2.5M in hexane (33 ml) in tetrahydrofuran (150 ml) at −70 C. under a nitrogen atmosphere. The reaction mixture was then warmed to 10 C., recooled to −70 and intermediate 24 (18.72 g) was slowly added maintaining the temperature below −70 C. After the addition was completed, the solution was maintained at that temperature for 15 min and then intermediate A (11.48 g), dissolved in THF (200 ml) was added over 30 mins maintaining the temperature below −70 C. The reaction was quenched after 5 minutes using a mixture of ammonium chloride (100 ml saturated solution) and hydrochloric acid (200 ml 10% solution) and extracted with ethyl acetate. The organic layer was washed with brine, dried, concentrated under reduced pressure and purified by flash chromatography using cyclohexane/ethyl acetate 85/15 to 30/70 as eluant, title compound (2.2 g., RF=0.65).

IR, CDCl$_3$ (cm$^{-1}$): 3418(NH), 1757(C=O lactam), 1718 (C=O), 1603 (C=O).

$^1$H-NMR 300 MHz CDCl$_3$, chemical shift (ppm, TMS): 7.32(m), 5.71 (s broad), 4.56 (s+m), 4.18(m), 3.99(m), 3.73(m), 3.6-3.5(m), 3.15(m), 2.87(dd), 2.30(m), 2.10(m), 1.80-1.50(m), 1.19(d), 0.86(s), 0.07(s+s);

EXAMPLE 17

(3S,4R)-3-[(R)-1-(t-butyldimethylsilyloxy)ethyl]-4-[(R)2'-[(S)6'-(2-azidoethoxy)-1'-oxocyclohexyl]]azetidin-2-one To a stirred solution of the Example 16 (3.7 g) in anhydrous dimethylformamide (20 ml), triphenylphosphine (2.6 g) and sodium azide (1.8 g) were added. Carbon tetrabromide 3.4 g) was then added over 10 min. After 2 hr. the resulting mixture was diluted with diethyl ether (50 ml) and washed three times with water (30 ml). The organic layer was dried and evaporated in vacuo. The residue was chromatographed on silica gel, using a ethyl acetate/cyclohexane 7/3 mixture as eluant, to afford the title compound as a colourless oil (2.6 g t.l.c. ethyl acetate/cyclohexane 9/1Rf=0.8).

IR (CDCl$_3$ V$_{max}$ (cm$^{-1}$) 3161 (N-H), 1759 (lactam), 1707 (C=O)

H$^1$-NMR (CDCl$_3$): 5.84 (sa), 4.18(m), 4.00(m), 3.71(t), 3.60(m), 3.49(m), 3.35(m), 3.12(m), 2.88(dd), 2.25(m), 2.20-2.00(m), 1.6(m), 1.22(d), 0.86(s), 0.06(s), 0.05(s).

EXAMPLE 18

(3S,4R)-3-[(R)-1-(t-butyldimethylsilyloxy)ethyl]-4-[(R)2'-[(S)6'-(2-azidoethoxy)-(R/S)-1'-hydroxycyclohexyl]]azetidin-2-one To a solution of the Example 17 (2.6 g) in methyl alcohol (70 ml) at −10 C., sodium borohydride (0.4 g) was added in 15 min. then, after 1 hr the mixture was quenched with a saturated solution of ammonium chloride (100 ml) and ethyl acetate (2×150 ml). The organic layer was dried and evaporated to afford the title compound (2.8 g) as a mixture of two diastereoisomers (t.l.c. Rf 0.6 ethyl acetate/cyclohexane 95/5).

IR (CDCl$_3$ V$_{max}$ (cm$^{-1}$) 3416 (N-H OH), 2108 (N$_3$) 1753 (lactam)

H$^1$-NMR (CDCl$_3$): 6.32(sa), 6.08(sa), 6.04(sa), 5.96(sa), 4.14(m), 4.00-3.00(m), 3.21(dd), 2.10-1.0(m), 1.32(d), 1.26(s), 0.90(s), 0.12(s).

EXAMPLE 19

(3S,4R)-3-[(R)-1-(t-butyldimethylsilyloxy)ethyl]-4-[(R)2'-[(S)6'-(2-allyloxycarbonylaminoethoxy)-1'-oxocyclohexyl]]azetidin-2-one To a solution of the Example 18 in anhydrous tetrahydrofuran (100 ml), triphenyl phosphine (1.6 g) was added, the mixture stirred at room temperature for 36 hr. and then water (0.09 ml) was added. After 12 hr the mixture was cooled at −5° C., an N-ethylpiperidine (0.9 ml) and allylchloroformate (0.8 ml) were added. After 3 hr the mixture was diluted with ethyl acetate (100 ml) and washed with a cooled 5% solution of hydrochloric acid (2×30 ml). The organic layer was dried, evaaporated and purified on silica gel using a ethyl acetate/cyclohexane 6/4 mixture as eluant. The material so obtained was dissolved in dichloromethane (30 ml), pyridinium chlorochromate (2.6 g) was added over 40 min and the mixture was refluxed. After 4 hr the mixture was filtered on celite and washed with a cooled 5% solution of hydrochloric acid (2×20 ml). The organic layer was dried and chromatographed on silica gel, using a ethyl acetate/cyclohexane 2/8 as eulant to afford the title compound as a colourless oil (0.75 g) t.l.c. ethyl acetate/cyclohexane 9/1 Rf=0.4)

EXAMPLE 20

Allyl (4S,8S,9R,10S, 12R)-4-methoxy-10-(1-(t-butyldimethylsilyloxy)ethyl)-11-oxo-1-azatricyclo[7.2.0.0$^{3,8}$]undec-2-ene-2-carboxylate Example 2 (0.5 g) was dissolved in methylene chloride (20 ml), anhydrous potassium carbonate (150 mg) added and the mixture stirred under nitrogen at 23°. Allyl oxalylchloride (0.2 ml) was added followed by triethylamine (0.2 ml). The reaction mixture stirred for 40 min and then filtered. The filtrate was washed with water (50 ml), a 5% solution of sodium hydrogen carbonate (50 ml) then brine and dried. The solution was concentrated under reduced pressure, and the oily residue dissolved in dry Xylene (30 ml). Triethyl phosphite (2 ml) was added and the mixture heated with stirring at 140° for 3 hr. The reaction mixture was cooled, concentration under reduced pressure and the residue chromatographed (eluants CH/EA; 8:2) to give the title compound (80 mg) as a colourless oil.

IR (CDCl$_3$) $\nu_{max}$ (cm$^{-1}$): 1772 ($\beta$-lactam), 1717 (C=O), 1634 (C=C)

H$^1$-NMR $\delta$ (CDCl$_3$): 6.0(m), 5.45 (m), 4.98 (m), 4.74 (m), 4.22 (m), 4.15 (dd), 3.28 (s), 3.22 (m), 3.21 (m), 2.07 (m), 1.84 (m), 1.66 (m), 1.6-1.2(m), 1.25 (d), 0.9 (s), 0.08 (s) ppm.

EXAMPLE 21

Allyl (4S,8S,9R,10S,12R)-4-methoxy-10-(1-hydroxy)ethyl)-11-oxo-1-azatricyclo[7.2.0.0$^{3,8}$]undec-2-ene-2-carboxylate Example 20 (80 mg) was dissolved in dry tetrahydrofuran (2 ml ), acetic acid (0.09 ml) was added followed by a 1M solution of tetrabutylammonium fluoride in tetrahydrofuran (0.45 ml). The reaction was stirred at 23° C. for 48 h then diluted with ethyl acetate (50 ml), extracted with a 5% solution of sodium hydrogen carbonate (2×50 ml) then with brine (50 ml). The residue after evaporation was purified by flash chromatography (eluants CH/EA mixtures) to obtain the title compound 20 mg as an oil.

IR (CDCl$_3$) $\nu_{max}$ (cm$^{-1}$): 3609 (O-H), 1772 (lactam), 1717 (C=O), 1642 (C=C)

H$^1$-NMR s (CDCl$_3$): 5.96 (m), 5.43 (m), 5.27 (m), 4.96 (m), 4.82 (m), 4.68 (m), 4.237 (m), 4.19 (dd), 3.25 (s), 3.28 (m), 3.20 (m), 2.08 (m), 1.9-1.8 (m), 1.65 (m), 1.45 (m), 1.32 (d) ppm.

EXAMPLE 22

Potassium (4S,8S,9R,10S,12R)-4-methoxy-10-(1-hydroxyethyl)-11-oxo-1-azatricyclo[7.2.0.0$^{3,8}$]undec-2-ene-2-carboxylate Example 21 (17 mg) was dissolved in dry tetrahydrofuran (2 ml) and to this was added a solution formed from a 0.5 molar solution of potassium 2-ethylhexanoate in ethyl acetate (0.1 ml), palladium (tetrakis)triphenylphosphine (5 mg) and triphenylphosphine (3 mg) in tetrahydrofuran (1.5 ml). The reaction was stirred at 23° C. for 20' and then diluted with a 1/1 mixture of ethyl ether and petroleum ether. The solid obtained was filtered, washed with ethyl ether/petroleum ether mixtures and dried to give the title compound (5 mg) as a white solid.

IR (CDCl$_3$) $\nu_{max}$ (cm$^{-1}$): 1751 ($\beta$-lactam), 1589 (C=O)

H$^1$-NMR $\delta$ (CDCL$_3$): 4.76 (m), 4.07 (m), 4.03 (m), 3.26 (dd), 3.08 (s), 2.99 (m), 1.84 (m), 1.71 (m), 1.53 (m), 1.41 (m), 1.2(m), 1.11 (d) ppm.

We claim:

1. Compounds of the formula (I)

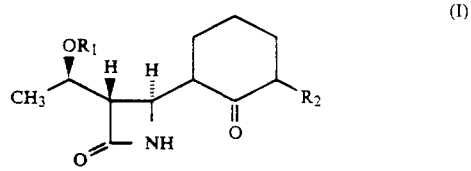

in which:

R$_1$ represents a hydroxyl protecting group; and
R$_2$ represents a hydrogen or halogen atom, an azido group, a C$_{1-3}$ alkyl group, a group (CH$_2$)$_m$OR$_3$ wherein m is zero or one and R$_3$ represents a hydrogen atom or a hydroxyl protecting group, or R$_2$ is an azidoethoxy group, a protected hydroxyethoxy group or a group XR$_4$ in which X is an oxygen atom or the group S(O)$_n$ in which n is zero, 1 or 2 and R$_4$ represents a C$_{1-5}$alkyl, C$_{3-7}$cycloalkyl or phenyl group or when X is oxygen or sulphur then R$_4$ may also represent the group AlkNR$_5$R$_6$ in which Alk represents a C$_{2-6}$ straight or branched alkylene chain and R$_5$ and R$_6$ independently represent a hydrogen atom or C$_{1-4}$alkyl group or R$_5$ and R$_6$ together with the nitrogen atom to which they are attached form a pyrrolidino or piperidino ring or the group NR$_5$R$_6$ represents a protected amino group, or R$_2$ represents the group (CH$_2$)$_m$NR$_7$R$_8$ in which m is zero or 1 and R$_7$ and R$_8$ independently represent a hydrogen atom or a C$_{1-4}$alkyl group or NR$_7$R$_8$ represents a protected amino group, or R$_2$ and the carbon atom to which it is attached represent a keto group;

and acid addition salts of such compounds containing basic centres.

2. Compounds as claimed in claim 1 in which R$_1$ is a trialkylsilyl group.

3. Compounds as claimed in claim 2 in which R$_1$ is a t-butyldimethylsilyl group.

4. Compounds as claimed in claim 1 in which R$_2$ is selected from hydrogen, iodine, azido, methyl, protected hydroxymethyl, methoxy, ethoxy, isopropoxy, cyclopentyloxy, methylthio, phenylthio, aminoethoxy, protected aminoethoxy, amino, protected amino, methylamino, protected methylamino, aminomethyl, protected aminomethyl, azidoethoxy, protected hydroxyethoxy, hydroxy and protected hydroxy.

5. Compounds as claimed in claim 4 wherein any hydroxy groups are protected as t-butyldimethylsilyloxy or benzyloxy groups and any amino groups are protected as allyloxycarbonylamino groups.

6. Compounds as claimed in claim 1 having the formula (Ib)

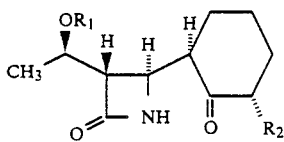

7. Compounds as claimed in claim 5 having the formula (Ib)

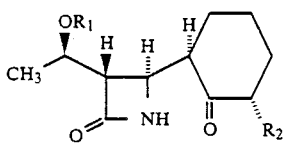

8. Compounds having the formula (Ib)

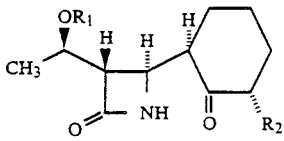

in which:
R₁ represents a hydroxyl protecting group; and
R₂ represents a hydrogen atom or a methoxy group.

9. Compounds as claimed in claim 2 in which $R_2$ is selected from hydrogen, iodine, azido, methyl, protected hydroxymethyl, methoxy, ethoxy, isopropoxy, cyclopentyloxy, methylthio, phenylthio, aminoethoxy, protected aminoethoxy, amino, protected amino, methylamino, protected methylamino, aminomethyl, protected aminomethyl, azidoethoxy, protected hydroxyethoxy, hydroxy and protected hydroxy.

10. Compounds as claimed in claim 3 in which $R_2$ is selected from hydrogen, iodine, azido, methyl, protected hydroxymethyl, methoxy, ethoxy, isopropoxy, cyclopentyloxy, methylthio, phenylthio, aminoethoxy, protected aminoethoxy, amino, protected amino, methylamino, protected methylamino, aminomethyl, protected aminomethyl, azidoethoxy, protected hydroxyethoxy, hydroxy and protected hydroxy.

11. Compounds as claimed in claim 2 having the formula (Ib)

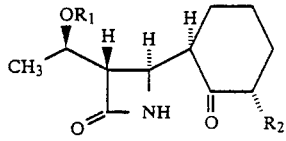

12. Compounds as claimed in claim 3 having the formula (Ib)

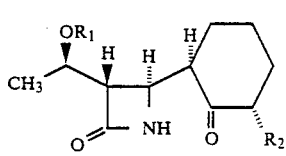

13. Compounds as claimed in claim 4 having the formula (Ib)

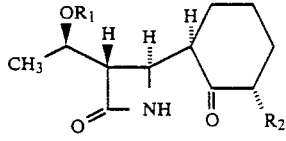

* * * * *